US009090668B2

(12) United States Patent
Suga et al.

(10) Patent No.: US 9,090,668 B2
(45) Date of Patent: Jul. 28, 2015

(54) PROCESS FOR SYNTHESIZING CYCLIC PEPTIDE COMPOUND

(75) Inventors: Hiroaki Suga, Tokyo (JP); Hiroshi Murakami, Tokyo (JP); Yuki Goto, Tokyo (JP); Yusuke Yamagishi, Tokyo (JP); Hiroshi Ashigai, Tokyo (JP); Yusuke Sako, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 700 days.

(21) Appl. No.: 12/593,221

(22) PCT Filed: Mar. 26, 2008

(86) PCT No.: PCT/JP2008/055771
§ 371 (c)(1),
(2), (4) Date: Feb. 26, 2010

(87) PCT Pub. No.: WO2008/117833
PCT Pub. Date: Oct. 2, 2008

(65) Prior Publication Data
US 2010/0168380 A1    Jul. 1, 2010

(30) Foreign Application Priority Data

Mar. 26, 2007 (JP) .................................. 2007-080141

(51) Int. Cl.
*C07K 7/56* (2006.01)
*C07K 7/06* (2006.01)
*C07K 7/08* (2006.01)
*C12N 15/67* (2006.01)
*C12P 21/02* (2006.01)

(52) U.S. Cl.
CPC ... *C07K 7/56* (2013.01); *C07K 7/06* (2013.01); *C07K 7/08* (2013.01); *C12N 15/67* (2013.01); *C12P 21/02* (2013.01)

(58) Field of Classification Search
None
See application file for complete search history.

(56) References Cited

U.S. PATENT DOCUMENTS

| 7,622,248 B2 * | 11/2009 | Suga et al. | 435/6.13 |
| 2009/0281280 A1 * | 11/2009 | Suga et al. | 530/333 |

FOREIGN PATENT DOCUMENTS

| JP | 2003-514572 A | 4/2003 |
| JP | 2005-528090 A | 9/2005 |
| WO | WO 01/38582 A1 | 5/2001 |
| WO | WO 01/66565 A2 | 9/2001 |
| WO | WO 03/070740 A1 | 8/2003 |

OTHER PUBLICATIONS

Seebeck et al. ("Ribosomal Synthesis of Dehydroalanine-Containing Peptides," JACS, 2006, 128, 7150-7151).*

Seebeck et al., Ribosomal Synthesis of Dehydroalanine-Containing Peptides; JACS, vol. 128, 7150-7151, 2006.*
Taki et al., Specific N-Terminal Biotinylation of a Protein In Vitro by a Chemically Modified tRNAbet can Support the Native Activity of the Translated Protein; J Biosci Bioeng, vol. 92, No. 2, 149-153, 2001.*
Taki et al., a novel immobilization method of an active protein via in vitro N-terminal specific incorporation system of nonnatural amino acids; NAR Supplement No. 1, p. 197-198, 2001.*
Punna et al., Head-to-Tail Peptide Cyclodimerization by Copper-Catalyzed Azide—Alkyne Cycloaddition; Angewandte Chemie, vol. 44, pp. 2215-2220, 2005.*
Lee et al., Ribozyme-catalyzed tRNA aminoacylation; Nature Structural Biology, vol. 7, No. 1, pp. 28-33, 2000.*
Bryan McIntosh et al., "Initiation of protein synthesis with fluorophore-Met-tRNAf and the involvement of IF-2", Biochimie, vol. 82, 2000, pp. 167-174.
Christine Mayer et al., "Anticodon Sequence Mutants of *Escherichia coli* Initiator tRNA: Effects of Overproduction of Aminoacyl-tRNA Synthetases, Methionyl-tRNA Formyltransferase, and Initiation Factor 2 on Activity in Initiation", Biochemistry, vol. 42, No. 17, 2003, pp. 4787-4799.
Hiroshi Murakami et al., "A highly flexible tRNA acylation method for non-natural polypeptide synthesis", Nature Methods, vol. 3, No. 5, May 2006, 357-359.
Hiroshi Murakami et al., "A Versatile tRNA Aminoacylation Catalyst Based on RNA", Chemistry & Biology, vol. 10, Jul. 2003, pp. 655-662.
Jerzy Olejnik et al., "N-terminal labeling of proteins using initiator tRNA", Methods, vol. 36, 2005, pp. 252-260.
Kade D. Roberts et al., "Efficient Synthesis of Thioether-Based Cyclic Peptide Libraries", Tetrahedron Letters, vol. 39, No. 45, Nov. 1998, pp. 8357-8360.
Lutz B. Giebel et al., "Screening of Cyclic Peptide Phage Libraries Identifies Ligands That Bind Streptavidin with High Affinities", Biochemistry, vol. 34, No. 47, 1995, pp. 15430-15435.
Masumi Taki et al., "Specific N-Terminal Biotinylation of a Protein In Vitro by a Chemically Modified tRNAfmet can Support the Native Activity of the Translated Protein", J. Bioscience and Bioengineering, vol. 92, No. 2, 2001, pp. 149-153.
Neal K. Williams et al., "In Vivo Protein Cyclization Promoted by a Circularly Permuted Synechocystis sp. PCC6803 DnaB Mini-intein", The Journal of Biological Chemistry, vol. 277, No. 10, Issue of Mar. 2000, pp. 7790-7798.

(Continued)

Primary Examiner — Anne Gussow
Assistant Examiner — Addison D Ault
(74) Attorney, Agent, or Firm — Birch, Stewart, Kolasch & Birch, LLP

(57) ABSTRACT

The objective is to provide a novel process for synthesizing a cyclic peptide compound. It is also an objective to provide a novel cyclic peptide compound. The novel process for synthesizing a cyclic peptide compound comprises the steps of: (1) translationally synthesizing a non-cyclic peptide compound having in a molecule a functional group 1 and a functional group 2, which are a pair of functional groups capable of reacting to form a bond, and (2) cyclizing the non-cyclic peptide compound by the reaction of the functional groups 1 and 2 to form a bond. The novel cyclic peptide compound can be synthesized by the process.

10 Claims, 15 Drawing Sheets

(56) References Cited

OTHER PUBLICATIONS

Norihito Muranaka et al., "Incorporation of Unnatural Non-•-Amino Acids into the N Terminus of Proteins in a Cell-Free Translation System", ChemBioChem, vol. 8, 2007, pp. 1650-1653.

Ranjan Chattapadhyay et al., "Initiation of in vivo protein synthesis with non-methionine amino acids", Biochemistry, vol. 29, No. 18, 1990, pp. 4263-4268.

Sadanand Gite et al., "Ultrasensitive Fluorescence-Based Detection of Nascent Proteins in Gels", Analytical Biochemistry, vol. 279, 2000, pp. 218-225.

Sergey Mamaev et al., "Cell-free N-terminal protein labeling using initiator suppressor tRNA", Analytical Biochemistry, vol. 326, 2004, pp. 25-32.

Steven W. Millward, et al., "A General Route for Post-Translational Cyclization of mRNA Display Libraries", J. Am. Chem. Soc., vol. 127, No. 41, 2005, pp. 14142-14143.

T. David Pallin, et al., "Cyclisation of Totally Unprotected Peptides in Aqueous Solution by Oxime Formation", J. Chem. Soc., Chem. Commun., 1995, pp. 2021-2022.

Umesh Varshney et al., "Initiation of protein synthesis from a termination codon", Proc. Natl. Acad. Sci. USA, vol. 87, Feb. 1990, pp. 1586-1590.

Vasanthi Ramachandiran et al., "Fluorophores at the N Terminus of Nascent Chloramphenicol Acetyltransferase Peptides Affect Translation and Movement through the Ribosome", J. Biol. Chem., vol. 275, No. 3, Jan. 2000, pp. 1781-1786.

Vsevolod V. Rostovtsev et al., "A Stepwise Huisgen Cycloaddition Process: Copper(I)-Catalyzed Regioselective 'Ligation' of Azides and Terminal Alkynes", Angew. Chem. Int. Ed., vol. 41, No. 14, 2002, 2596-2599.

Wieslaw Kudlicki et al., "Chaperone-dependent Folding and Activation of Ribosome-bound Nascent Rhodanese", J. Mol. Biol., vol. 244, 1994, pp. 319-331.

Yamaguchi, Y. et al., A novel "click chemistry" for posttranslational modification and cyclization of peptides, The Chemical Society of Japan Dai 87 Shunki Nenkai Koen Yokoshu II, Mar. 12, 2007, p. 1334, Abst. No. 4K1-10.

Yuki Goto et al., "Reprogramming the Translation Initiation for the Synthesis of Physiologically Stable Cyclic Peptides", ACS Chem. Biol., vol. 3, No. 2, 2008, pp. 120-129.

Extended European Search Report issued on Oct. 11, 2010.

Goto Yuki et al, "Translation initiation by using N-acylaminoacyl tRNAs.", Nucleic Acids Symposium Series, (2004) 2006, No. 50, 2006, pp. 293-294. XP002600243.

Hendrickson Tamara L et al, "Incorporation of nonnatrual amino acids into proteins", Annual Review of Biochemistry, vol. 73, Mar. 26, 2004, pp. 147-176. XP0009093569.

Murakami Hiroshi et al, "Flexizyme as a versatile tRNA acylation catalyst and the application for translation.", Nucleic Acids Symposium Series, (2004) 2006, No. 50, 2006, pp. 35-36. XP002600244.

Seebeck Florian P et al, "Ribosomal synthesis of dehydroalanine-containing peptides.", Journal of American Chemical Society, vol. 128, No. 22, Jun. 2006, pp. 7150-7151.

Yamagishi, Y. et al., A novel "click chemistry" for posttranslational modification and cyclization of peptides, The Chemical Society of Japan Dai 87 Shunki Nenkai Koen Yokoshu II, Mar. 12, 2007, p. 1334, Abst. No. 4K1-10, with English translation.

\* cited by examiner

Figure 7

Urotensin II analog YS9
MPDBFWKYCV
          |___S
              |
              S Urotensin II
ETPDCFWKYCV
         |__S-S__|

SEQUENCE LISTING

<160> NUMBER OF SEQ ID NOS: 61

<210> SEQ ID NO 1
<211> LENGTH: 77
<212> TYPE: RNA
<213> ORGANISM: Artificial Sequence
<220> FEATURE:
<223> OTHER INFORMATION: Synthetic: initiator tRNA (tRNA fMet)

<400> SEQUENCE: 1
ggcggggugg agcagccugg uagcucgucg ggcucauaac ccgaagaucg ucgguucaaa    60
uccggccccc gcaacca                                                   77

<210> SEQ ID NO 2
<211> LENGTH: 77
<212> TYPE: RNA
<213> ORGANISM: Artificial Sequence
<220> FEATURE:
<223> OTHER INFORMATION: Synthetic: initiator tRNA with substituted
      anticodon
<220> FEATURE:
<221> NAME/KEY: misc_feature
<222> LOCATION: (35)..(37)
<223> OTHER INFORMATION: anticodon
<220> FEATURE:
<221> NAME/KEY: misc_feature
<222> LOCATION: (35)..(37)
<223> OTHER INFORMATION: n stand for any base

<400> SEQUENCE: 2
ggcggggugg agcagccugg uagcucgucg ggcunnnaac ccgaagaucg ucgguucaaa    60
uccggccccc gcaacca                                                   77

<210> SEQ ID NO 3
<211> LENGTH: 45
<212> TYPE: RNA
<213> ORGANISM: Artificial Sequence
<220> FEATURE:
<223> OTHER INFORMATION: Synthetic: ribozyme I

<400> SEQUENCE: 3
ggaucgaaag auuccgcgg ccccgaaagg ggauuagcgu uaggu                      45

<210> SEQ ID NO 4
<211> LENGTH: 46
<212> TYPE: RNA
<213> ORGANISM: Artificial Sequence
<220> FEATURE:
<223> OTHER INFORMATION: Synthetic: ribozyme II

<400> SEQUENCE: 4
ggaucgaaag auuccgcau ccccgaaagg guacauggcg uuaggu                     46

<210> SEQ ID NO 5
<211> LENGTH: 49
<212> TYPE: DNA
<213> ORGANISM: Artificial Sequence
<220> FEATURE:
<223> OTHER INFORMATION: Synthetic: P1

<400> SEQUENCE: 5
gtaatacgac tcactatagg cggggtggag cagcctggta gctcgtcgg                 49

<210> SEQ ID NO 6
<211> LENGTH: 44
<212> TYPE: DNA
<213> ORGANISM: Artificial Sequence
<220> FEATURE:
<223> OTHER INFORMATION: Synthetic: P2

<400> SEQUENCE: 6
gaaccgacga tcttcgggtt atgagcccga cgagctacca ggct                      44

```
<210> SEQ ID NO 7
<211> LENGTH: 25
<212> TYPE: DNA
<213> ORGANISM: Artificial Sequence
<220> FEATURE:
<223> OTHER INFORMATION: Synthetic: P3

<400> SEQUENCE: 7
gcatatgtaa tacgactcac tatag                                         25

<210> SEQ ID NO 8
<211> LENGTH: 38
<212> TYPE: DNA
<213> ORGANISM: Artificial Sequence
<220> FEATURE:
<223> OTHER INFORMATION: Synthetic: P4

<400> SEQUENCE: 8
tggttgcggg ggccggattt gaaccgacga tcttcggg                           38

<210> SEQ ID NO 9
<211> LENGTH: 20
<212> TYPE: DNA
<213> ORGANISM: Artificial Sequence
<220> FEATURE:
<223> OTHER INFORMATION: Synthetic: P5

<400> SEQUENCE: 9
tggttgcggg ggccggattt                                               20

<210> SEQ ID NO 10
<211> LENGTH: 49
<212> TYPE: DNA
<213> ORGANISM: Artificial Sequence
<220> FEATURE:
<223> OTHER INFORMATION: Synthetic: P6

<400> SEQUENCE: 10
gtaatacgac tcactatagg ctctgtagtt cagtcggtag aacggcgga               49

<210> SEQ ID NO 11
<211> LENGTH: 43
<212> TYPE: DNA
<213> ORGANISM: Artificial Sequence
<220> FEATURE:
<223> OTHER INFORMATION: Synthetic: P7
<220> FEATURE:
<221> NAME/KEY: misc_feature
<222> LOCATION: (21)..(23)
<223> OTHER INFORMATION: n stand for any base

<400> SEQUENCE: 11
gaaccagtga catacggatt nnnagtccgc cgttctaccg act                     43

<210> SEQ ID NO 12
<211> LENGTH: 38
<212> TYPE: DNA
<213> ORGANISM: Artificial Sequence
<220> FEATURE:
<223> OTHER INFORMATION: Synthetic: P8

<400> SEQUENCE: 12
tggcggctct gactggactc gaaccagtga catacgga                           38

<210> SEQ ID NO 13
<211> LENGTH: 20
<212> TYPE: DNA
```

```
<213> ORGANISM: Artificial Sequence
<220> FEATURE:
<223> OTHER INFORMATION: Synthetic: P9

<400> SEQUENCE: 13
tggttgcggg ggccggattt                                              20

<210> SEQ ID NO 14
<211> LENGTH: 94
<212> TYPE: RNA
<213> ORGANISM: Artificial Sequence
<220> FEATURE:
<223> OTHER INFORMATION: Synthetic: tRNA (tRNA Asn NNN)
<220> FEATURE:
<221> NAME/KEY: misc_feature
<222> LOCATION: (52)..(54)
<223> OTHER INFORMATION: anticodon
<220> FEATURE:
<221> NAME/KEY: misc_feature
<222> LOCATION: (52)..(54)
<223> OTHER INFORMATION: n stand for any base

<400> SEQUENCE: 14
guaauacgac ucacuauagc cucuguaguu cagucgguag aacggcggac unnnaauccg    60
uaugucacug guucgagucc agucagaggc acca                               94

<210> SEQ ID NO 15
<211> LENGTH: 119
<212> TYPE: DNA
<213> ORGANISM: Artificial Sequence
<220> FEATURE:
<223> OTHER INFORMATION: Synthetic: template DNA 1

<400> SEQUENCE: 15
gcatatgtaa tacgactcac tatagggtta actttaacaa ggagaaaaac atgtttgaag    60
gttatgacaa tacctttccg tgcctcgact acaaggacga cgacgacaag taagcttcg   119

<210> SEQ ID NO 16
<211> LENGTH: 92
<212> TYPE: DNA
<213> ORGANISM: Artificial Sequence
<220> FEATURE:
<223> OTHER INFORMATION: Synthetic: template DNA 2

<400> SEQUENCE: 16
gcatatgtaa tacgactcac tatagggtta actttaacaa ggagaaaaac atgtttgaag    60
gttatgacaa tacctttccg tgctaagctt cg                                 92

<210> SEQ ID NO 17
<211> LENGTH: 119
<212> TYPE: DNA
<213> ORGANISM: Artificial Sequence
<220> FEATURE:
<223> OTHER INFORMATION: Synthetic: template DNA 3

<400> SEQUENCE: 17
gcatatgtaa tacgactcac tatagggtta actttaacaa ggagaaaaac atgtttgaag    60
gttatgacaa tacctttccg tgcctcgact acaaggacga cgacgacaag taagcttcg   119

<210> SEQ ID NO 18
<211> LENGTH: 82
<212> TYPE: DNA
<213> ORGANISM: Artificial Sequence
<220> FEATURE:
<223> OTHER INFORMATION: Synthetic: template DNA 4
```

<400> SEQUENCE: 18
taatacgact cactataggg ttaactttaa caaggagaaa aacatgccgg acctcttctg    60
gaagtactgt gtttaagctt cg                                            82

<210> SEQ ID NO 19
<211> LENGTH: 82
<212> TYPE: DNA
<213> ORGANISM: Artificial Sequence
<220> FEATURE:
<223> OTHER INFORMATION: Synthetic: template DNA 5

<400> SEQUENCE: 19
taatacgact cactataggg ttaactttaa caaggagaaa aacatgccgg actgtttctg    60
gaagtactgt gtttaagctt cg                                            82

<210> SEQ ID NO 20
<211> LENGTH: 114
<212> TYPE: DNA
<213> ORGANISM: Artificial Sequence
<220> FEATURE:
<223> OTHER INFORMATION: Synthetic: template DNA 6

<400> SEQUENCE: 20
taatacgact cactataggg ctttaataag gagaaaaaca tgaccccgga ctgtttctgg    60
aagtactgtg ttctcgaaga agactacaag gacgacgacg acaagtaagc ttcg         114

<210> SEQ ID NO 21
<211> LENGTH: 106
<212> TYPE: DNA
<213> ORGANISM: Artificial Sequence
<220> FEATURE:
<223> OTHER INFORMATION: Synthetic: template DNA 7

<400> SEQUENCE: 21
taatacgact cactataggg tgatccaact ttaataagga ggtataccaa tgagtggcgg    60
cccgggcggc aacgattata aagatgatga tgataaataa gcttcg                  106

<210> SEQ ID NO 22
<211> LENGTH: 116
<212> TYPE: DNA
<213> ORGANISM: Artificial Sequence
<220> FEATURE:
<223> OTHER INFORMATION: Synthetic: template DNA 8

<400> SEQUENCE: 22
cgtatactaa tacgactcac tagggttaa actttaacaa ggagaaaaac atggttggtg    60
caggtgcagt tggtgcactc aacgactaca aggacgacga cgacaagtaa gcttcg       116

<210> SEQ ID NO 23
<211> LENGTH: 95
<212> TYPE: DNA
<213> ORGANISM: Artificial Sequence
<220> FEATURE:
<223> OTHER INFORMATION: Synthetic: template DNA 9

<400> SEQUENCE: 23
cgtatactaa tacgactcac tagggttaa actttaacaa ggagaaaaac atgcgaaccc    60
gaagtccagt taacctcggt atcgactaag cttcg                              95

<210> SEQ ID NO 24

```
<211> LENGTH: 89
<212> TYPE: DNA
<213> ORGANISM: Artificial Sequence
<220> FEATURE:
<223> OTHER INFORMATION: Synthetic: template DNA 10

<400> SEQUENCE: 24
cgtatactaa tacgactcac tatagggtta actttaacaa ggagaaaaac atgcgaaccc      60
gaagtccagt aacatcgac taagcttcg                                         89

<210> SEQ ID NO 25
<211> LENGTH: 83
<212> TYPE: DNA
<213> ORGANISM: Artificial Sequence
<220> FEATURE:
<223> OTHER INFORMATION: Synthetic: template DNA 11

<400> SEQUENCE: 25
cgtatactaa tacgactcac tatagggtta actttaacaa ggagaaaaac atgcgaaccc      60
gaagtccaat cgactaagct tcg                                              83

<210> SEQ ID NO 26
<211> LENGTH: 77
<212> TYPE: DNA
<213> ORGANISM: Artificial Sequence
<220> FEATURE:
<223> OTHER INFORMATION: Synthetic: template DNA 12

<400> SEQUENCE: 26
cgtatactaa tacgactcac tatagggtta actttaacaa ggagaaaaac atgcgaaccc      60
gaatcgacta agcttcg                                                     77

<210> SEQ ID NO 27
<211> LENGTH: 12
<212> TYPE: PRT
<213> ORGANISM: Unknown
<220> FEATURE:
<223> OTHER INFORMATION: Synthetic: Peptide binding to SH2 domain of
      Grb7
<220> FEATURE:
<221> NAME/KEY: DISULFID
<222> LOCATION: (1)..(12)

<400> SEQUENCE: 27

Cys Trp Phe Glu Gly Tyr Asp Asn Thr Phe Pro Cys
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic: Peptide region of compound of
      formula 16

<400> SEQUENCE: 28

Trp Phe Glu Gly Tyr Asp Asn Thr Phe Pro Cys
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Synthetic: Peptide region of compound of
      formula 11
```

```
<220> FEATURE:
<221> NAME/KEY: MISC_FEATURE
<222> LOCATION: (2)..(2)
<223> OTHER INFORMATION: Xaa = derived from tyrosine derivative
<220> FEATURE:
<221> NAME/KEY: MISC_FEATURE
<222> LOCATION: (8)..(8)
<223> OTHER INFORMATION: Xaa = derived from tryptophan derivative

<400> SEQUENCE: 29

Met Xaa Gly Gly Pro Gly Gly Xaa
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic: Peptide region of compound of
      formula 12
<220> FEATURE:
<221> NAME/KEY: MISC_FEATURE
<222> LOCATION: (1)..(1)
<223> OTHER INFORMATION: Xaa = derived from phenylalanine derivative
<220> FEATURE:
<221> NAME/KEY: MISC_FEATURE
<222> LOCATION: (9)..(9)
<223> OTHER INFORMATION: Xaa = derived from tryptophan derivative

<400> SEQUENCE: 30

Xaa Val Gly Ala Gly Ala Gly Ala Xaa
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic: Peptide region of compound of
      formula 35
<220> FEATURE:
<221> NAME/KEY: MISC_FEATURE
<222> LOCATION: (4)..(4)
<223> OTHER INFORMATION: Xaa = derived from 2,4-diaminobutyric acid
      derivative

<400> SEQUENCE: 31

Met Pro Asp Xaa Phe Trp Lys Tyr Cys Val
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Synthetic: Peptide region of compound of
      formula 36
<220> FEATURE:
<221> NAME/KEY: MISC_FEATURE
<222> LOCATION: (5)..(5)
<223> OTHER INFORMATION: Xaa = derived from 2-amino-6-azido-hexanoic
      acid
<220> FEATURE:
<221> NAME/KEY: MISC_FEATURE
<222> LOCATION: (12)..(12)
<223> OTHER INFORMATION: Xaa = derived from 2-amino-4-pentynoic acid

<400> SEQUENCE: 32

Met Lys Lys Lys Xaa Gly Phe Gly Pro Gly Gly Xaa
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Synthetic: Peptide region of compound of
      formula 38
<220> FEATURE:
<221> NAME/KEY: MISC_FEATURE
<222> LOCATION: (1)..(1)
<223> OTHER INFORMATION: Xaa = derived from phenylalanine derivative
<220> FEATURE:
<221> NAME/KEY: MISC_FEATURE
<222> LOCATION: (11)..(11)
<223> OTHER INFORMATION: Xaa = derived from tryptophan derivative

<400> SEQUENCE: 33

Xaa Arg Thr Arg Ser Pro Val Asn Leu Gly Xaa Asp
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic: Peptide region of compound of
      formula 40
<220> FEATURE:
<221> NAME/KEY: MISC_FEATURE
<222> LOCATION: (1)..(1)
<223> OTHER INFORMATION: Xaa = derived from phenylalanine derivative
<220> FEATURE:
<221> NAME/KEY: MISC_FEATURE
<222> LOCATION: (9)..(9)
<223> OTHER INFORMATION: Xaa = derived from tryptophan derivative

<400> SEQUENCE: 34

Xaa Arg Thr Arg Ser Pro Val Asn Xaa Asp
1               5                   10

<210> SEQ ID NO 35
<211> LENGTH: 8
<212> TYPE: PRT
<213> ORGANISM: Artificial Sequence
<220> FEATURE:
<223> OTHER INFORMATION: Synthetic: Peptide region of compound of
      formula 42
<220> FEATURE:
<221> NAME/KEY: MISC_FEATURE
<222> LOCATION: (1)..(1)
<223> OTHER INFORMATION: Xaa = derived from phenylalanine derivative
<220> FEATURE:
<221> NAME/KEY: MISC_FEATURE
<222> LOCATION: (7)..(7)
<223> OTHER INFORMATION: Xaa = derived from tryptophan derivative

<400> SEQUENCE: 35

Xaa Arg Thr Arg Ser Pro Xaa Asp
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic: Peptide region of compound of
      formula 44
<220> FEATURE:
<221> NAME/KEY: MISC_FEATURE
<222> LOCATION: (1)..(1)
<223> OTHER INFORMATION: Xaa = derived from phenylalanine derivative
<220> FEATURE:
<221> NAME/KEY: MISC_FEATURE
```

```
<222> LOCATION: (5)..(5)
<223> OTHER INFORMATION: Xaa = derived from tryptophan derivative

<400> SEQUENCE: 36

Xaa Arg Thr Arg Xaa Asp
1               5

<210> SEQ ID NO 37
<211> LENGTH: 45
<212> TYPE: RNA
<213> ORGANISM: Artificial Sequence
<220> FEATURE:
<223> OTHER INFORMATION: Synthetic

<400> SEQUENCE: 37
ggaucgaaag auuccgcgg ccccgaaagg ggauuagcgu uaggu         45

<210> SEQ ID NO 38
<211> LENGTH: 46
<212> TYPE: RNA
<213> ORGANISM: Artificial Sequence
<220> FEATURE:
<223> OTHER INFORMATION: Synthetic

<400> SEQUENCE: 38
ggaucgaaag auuccgcau ccccgaaagg guacauggcg uuaggu        46

<210> SEQ ID NO 39
<211> LENGTH: 36
<212> TYPE: RNA
<213> ORGANISM: Artificial Sequence
<220> FEATURE:
<223> OTHER INFORMATION: Synthetic

<400> SEQUENCE: 39
auguuugaag guuaugacaa uaccuuuccg ugccuc                  36

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Phe Asp Tyr Lys Asp Asp Asp Lys
1               5

<210> SEQ ID NO 41
<211> LENGTH: 36
<212> TYPE: RNA
<213> ORGANISM: Artificial Sequence
<220> FEATURE:
<223> OTHER INFORMATION: Synthetic

<400> SEQUENCE: 41
auguuugaag guuaugacaa uaccuuuccg ugcuaa                  36

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42
```

```
Glu Thr Pro Asp Cys Phe Trp Lys Tyr Cys Val
1               5                   10
```

<210> SEQ ID NO 43
<211> LENGTH: 12
<212> TYPE: PRT
<213> ORGANISM: Artificial Sequence
<220> FEATURE:
<223> OTHER INFORMATION: Synthetic

<400> SEQUENCE: 43

```
Met Phe Glu Gly Tyr Asp Asx Thr Phe Pro Cys Leu
1               5                   10
```

<210> SEQ ID NO 44
<211> LENGTH: 10
<212> TYPE: PRT
<213> ORGANISM: Artificial Sequence
<220> FEATURE:
<223> OTHER INFORMATION: Synthetic

<400> SEQUENCE: 44

```
Met Pro Asp Cys Phe Trp Lys Tyr Cys Val
1               5                   10
```

<210> SEQ ID NO 45
<211> LENGTH: 10
<212> TYPE: PRT
<213> ORGANISM: Artificial Sequence
<220> FEATURE:
<223> OTHER INFORMATION: Synthetic

<400> SEQUENCE: 45

```
Met Pro Asp Leu Phe Trp Lys Tyr Cys Val
1               5                   10
```

<210> SEQ ID NO 46
<211> LENGTH: 12
<212> TYPE: PRT
<213> ORGANISM: Artificial Sequence
<220> FEATURE:
<223> OTHER INFORMATION: Synthetic

<400> SEQUENCE: 46

```
Met Lys Lys Lys Leu Gly Phe Gly Pro Gly Gly Thr
1               5                   10
```

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
atgagtggcg gcccgggcgg caactaa                                        27

<210> SEQ ID NO 48
<211> LENGTH: 8
<212> TYPE: PRT
<213> ORGANISM: Artificial Sequence
<220> FEATURE:
<223> OTHER INFORMATION: Synthetic

<400> SEQUENCE: 48

```
Met Ser Gly Gly Pro Gly Gly Asn
1               5
```

<210> SEQ ID NO 49
<211> LENGTH: 8
<212> TYPE: PRT
<213> ORGANISM: Artificial Sequence
<220> FEATURE:
<223> OTHER INFORMATION: Synthetic

<400> SEQUENCE: 49

Met Tyr Gly Gly Pro Gly Gly Trp
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic

<400> SEQUENCE: 50

Phe Val Gly Ala Gly Ala Gly Ala Trp
1               5

<210> SEQ ID NO 51
<211> LENGTH: 82
<212> TYPE: DNA
<213> ORGANISM: Artificial Sequence
<220> FEATURE:
<223> OTHER INFORMATION: Synthetic

<400> SEQUENCE: 51
cgaagcttaa acacagtact tccagaagag gtccggcatg ttttctcct tgttaaagtt      60 aaccctatag tgagtcgtat ta                                              82

<210> SEQ ID NO 52
<211> LENGTH: 82
<212> TYPE: DNA
<213> ORGANISM: Artificial Sequence
<220> FEATURE:
<223> OTHER INFORMATION: Synthetic

<400> SEQUENCE: 52
cgaagcttaa acacagtact tccagaaaca gtccggcatg ttttctcct tgttaaagtt      60 aaccctatag tgagtcgtat ta                                              82

<210> SEQ ID NO 53
<211> LENGTH: 114
<212> TYPE: DNA
<213> ORGANISM: Artificial Sequence
<220> FEATURE:
<223> OTHER INFORMATION: Synthetic

<400> SEQUENCE: 53
cgaagcttac ttgtcgtcgt cgtccttgta gtcttcttcg agaacacagt acttccagaa     60
acagtccggg gtcatgtttt tctccttatt aaagccctat agtgagtcgt atta          114

<210> SEQ ID NO 54
<211> LENGTH: 106
<212> TYPE: DNA
<213> ORGANISM: Artificial Sequence
<220> FEATURE:
<223> OTHER INFORMATION: Synthetic

<400> SEQUENCE: 54

```
cgaagcttat ttatcatcat catctttata atcgttgccg cccgggccgc cactcattgg    60
tatacctcct tattaaagtt ggatcaccct atagtgagtc gtatta                  106
```

<210> SEQ ID NO 55
<211> LENGTH: 116
<212> TYPE: DNA
<213> ORGANISM: Artificial Sequence
<220> FEATURE:
<223> OTHER INFORMATION: Synthetic

<400> SEQUENCE: 55

```
cgaagcttac ttgtcgtcgt cgtccttgta gtcgttgagt gcaccaactg cacctgcacc    60
aaccatgttt ttctccttgt taaagttaac cctatagtga gtcgtattag tatacg       116
```

<210> SEQ ID NO 56
<211> LENGTH: 95
<212> TYPE: DNA
<213> ORGANISM: Artificial Sequence
<220> FEATURE:
<223> OTHER INFORMATION: Synthetic

<400> SEQUENCE: 56

```
cgaagcttag tcgataccga ggttaactgg acttcgggtt cgcatgtttt tctccttgtt    60
aaagttaacc ctatagtgag tcgtattagt atacg                              95
```

<210> SEQ ID NO 57
<211> LENGTH: 89
<212> TYPE: DNA
<213> ORGANISM: Artificial Sequence
<220> FEATURE:
<223> OTHER INFORMATION: Synthetic

<400> SEQUENCE: 57

```
cgaagcttag tcgatgttaa ctggacttcg ggttcgcatg ttttctcct tgttaaagtt    60 aaccctatag tgagtcgtat tagtatacg                                     89
```

<210> SEQ ID NO 58
<211> LENGTH: 83
<212> TYPE: DNA
<213> ORGANISM: Artificial Sequence
<220> FEATURE:
<223> OTHER INFORMATION: Synthetic

<400> SEQUENCE: 58

```
cgaagcttag tcgattggac ttcgggttcg catgtttttc tccttgttaa agttaaccct    60
atagtgagtc gtattagtat acg                                           83
```

<210> SEQ ID NO 59
<211> LENGTH: 77
<212> TYPE: DNA
<213> ORGANISM: Artificial Sequence
<220> FEATURE:
<223> OTHER INFORMATION: Synthetic

<400> SEQUENCE: 59

```
cgaagcttag tcgattcggg ttcgcatgtt tttctccttg ttaaagttaa ccctatagtg    60
agtcgtatta gtatacg                                                  77
```

<210> SEQ ID NO 60
<211> LENGTH: 4
<212> TYPE: PRT
<213> ORGANISM: Artificial Sequence

```
<220> FEATURE:
<223> OTHER INFORMATION: Synthetic peptide region of compound of formula
      14

<400> SEQUENCE: 60

Met Lys Lys Lys
1

<210> SEQ ID NO 61
<211> LENGTH: 6
<212> TYPE: PRT
<213> ORGANISM: Artificial Sequence
<220> FEATURE:
<223> OTHER INFORMATION: Synthetic peptide region of compound of formula
      14

<400> SEQUENCE: 61

Gly Phe Gly Pro Gly Gly
1               5
```

PROCESS FOR SYNTHESIZING CYCLIC PEPTIDE COMPOUND

TECHNICAL FIELD

The present invention relates to a novel process for synthesizing a cyclic peptide compound. In particular, the present invention relates to a novel process for synthesizing a cyclic peptide compound, comprising synthesizing a non-cyclic peptide compound by use of a cell-free translation system followed by cyclization of the non-cyclic peptide compound; one feature of the process is to use a ribozyme that enables aminoacylation of a tRNA with any amino acid compound. The present invention also relates to a novel cyclic peptide compound that can be synthesized by the foregoing process.

BACKGROUND ART

There are a large number of peptide compounds having a cyclic structure (cyclic peptide compounds) in nature, and it is known that they have various physiological activities. For example, Urotensin II and somatostatins are cyclic peptide compounds having a disulfide bond in a ring, and it is known that Urotensin II and somatostatins have, for example, vasoconstriction action and inhibitory action on growth hormone (GH) secretion of hypophysis, respectively.

Cyclic peptide compounds exhibit various types of action in vivo, and interest in novel action and the like has motivated synthesis of cyclic peptide compounds having a novel structure. This has encouraged development of novel processes for the synthesis of cyclic peptide compounds.

It is known that the disulfide bond in the rings of the cyclic peptide compounds such as Urotensin II is relatively unstable in vivo. Thus, substitution of the disulfide bond in the rings of the cyclic peptide compounds with a bond of other forms has been carried out to synthesize cyclic peptide compounds having increased stability in vivo. For example, a disulfide bond of a peptide of formula (15) (SEQ ID NO: 27) isolated as a peptide binding to the SH2 domain of the Grb7 protein is substituted with a thioeter bond to synthesize a compound of formula (16) (SEQ ID NO: 28).

[Formula 1]

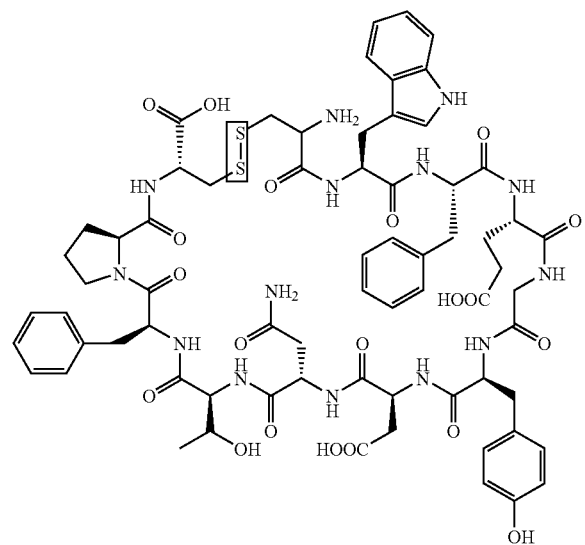

(15)

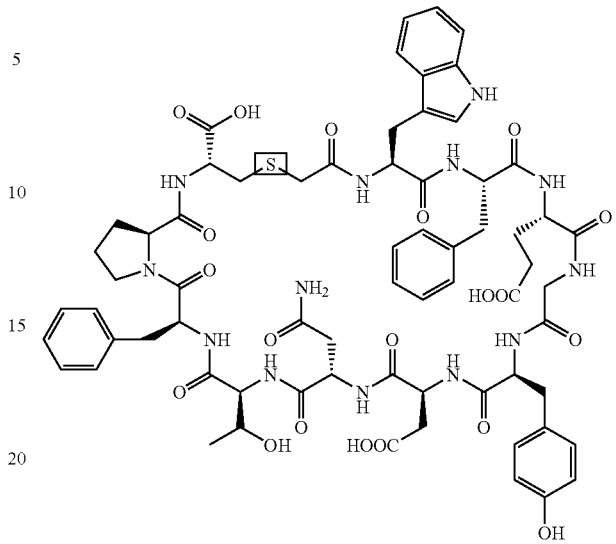

(16)

This has also encouraged the development of processes for the synthesis of cyclic peptide compounds.

However, forming a disulfide bridge via cysteine is the only way available in current processes for the translational synthesis of cyclic peptide compounds, and it is difficult to maintain a cyclic form of peptides under reduction conditions or in human blood. This brings a problem that peptides changed into a linear form have significantly low in vivo stability, compared with the original cyclic peptides. Thus, there have been demands for development of novel processes for synthesizing cyclic peptides that maintain in vivo stability.

Further, ribozymes having a wide range of tRNA aminoacylation activities, and aminoacylation of tRNAs using the ribozymes are known.

Patent document 1: JPA 2003-514572
Patent document 2: JPA 2005-528090
Non-patent document 1: H. Murakami, H. Saito, and H. Suga (2003) "A versatile tRNA aminoacylation catalyst based on RNA" Chemistry & Biology, Vol. 10, 655-662
Non-patent document 2: H. Murakami, A. Ohta, H. Ashigai, H. Suga (2006) "The flexizyme system: a highly flexible tRNA aminoacylation tool for the synthesis of nonnatural peptides" Nature Methods 3, 357-359

DISCLOSURE OF THE INVENTION

Technical Problem

An object of the present invention is to provide a novel process for synthesizing a cyclic peptide compound. It is also an object of the present invention to provide a novel cyclic peptide compound.

Technical Solution

The present inventors studied to achieve the above objective. Consequently, the inventors found that a cyclic peptide compound could be efficiently synthesized by translationally synthesizing a non-cyclic peptide compound containing a pair of functional groups capable of reacting to form a bond and thereafter cyclizing the non-cyclic peptide compound. By this finding, the present invention was completed.

Specifically, the present invention includes
1. A process for synthesizing a cyclic peptide compound, comprising the steps of: (1) translationally synthesizing a non-cyclic peptide compound having a functional group 1 and a functional group 2, which are a pair of functional groups capable of reacting to form a bond; and (2) cyclizing the non-cyclic peptide compound by the reaction of the functional group 1 and the functional group 2 to form a bond;
2. The process of 1, wherein the step (1) comprises the substeps of: (a) providing a ribozyme capable of catalyzing an aminoacylation reaction of a tRNA with any amino acid compound; (b) providing an initiator tRNA and an amino acid compound having the functional group 1 for use as a substrate for the acylation reaction by the ribozyme; (c) performing an aminoacylation of the initiator tRNA with the amino acid compound having the functional group 1 using the ribozyme; (d) providing a cell-free translation system which contains at least an amino acid compound having the functional group 2 and a tRNA to be aminoacylated with the amino acid compound having the functional group 2, and is free of methionine; (e) providing a template DNA for forming an mRNA having at desired positions a codon corresponding to an anticodon of the initiator tRNA, and a codon corresponding to an anticodon of the tRNA to be aminoacylated with the amino acid compound having the functional group 2; and (f) adding the aminoacylated initiator tRNA obtained in the substep (c) and the template DNA to the cell-free translation system to synthesize the non-cyclic peptide compound;
3. The process of 1, wherein the step (1) comprises the substeps of: (a) providing a ribozyme capable of catalyzing an aminoacylation reaction of a tRNA with any amino acid compound; (b) providing an initiator tRNA and an amino acid compound having the functional group 1 for use as a substrate for the acylation reaction by the ribozyme; (c) performing an aminoacylation of the initiator tRNA with the amino acid compound having the functional group 1 using the ribozyme; (d) providing a tRNA having an orthogonal relationship to a natural aminoacyl-tRNA synthetase present in a cell-free translation system, and an amino acid compound having the functional group 2, for use as a substrate for the acylation reaction by the ribozyme; (e) performing an aminoacylation of the tRNA with the amino acid compound having the functional group 2 using the ribozyme; (f) providing a cell-free translation system free of methionine; (g) providing a template DNA for forming an mRNA having at desired positions a codon corresponding to an anticodon of the initiator tRNA, and a codon corresponding to an anticodon of the tRNA; and (h) adding the aminoacylated initiator tRNA obtained in the substep (c), the tRNA aminoacylated in the substep (e) with the amino acid compound having the functional group 2, and the template DNA to the cell-free translation system to synthesize the non-cyclic peptide compound;
4. The process of 1, wherein the step (1) comprises the substeps of: (a) providing a ribozyme capable of catalyzing an aminoacylation reaction of a tRNA in any amino acid compound; (b) providing a tRNA having an orthogonal relationship to a natural aminoacyl-tRNA synthetase present in a cell-free translation system, and an amino acid compound having the functional group 1, for use as a substrate for the acylation reaction by the ribozyme; (c) performing an aminoacylation of the tRNA with the amino acid compound having the functional group 1 using the ribozyme; (d) providing a cell-free translation system containing at least an amino acid compound having the functional group 2, a tRNA to be aminoacylated with the amino acid compound having the functional group 2, an initiator tRNA, methionine, and a methionyl-tRNA synthetase; (e) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and (f) adding the aminoacylated tRNA obtained in the substep (c) and the template DNA to the cell-free translation system to synthesize the non-cyclic peptide compound;
5. The process of 1, wherein the step (1) comprises the substeps of: (a) providing a ribozyme capable of catalyzing an aminoacylation reaction of a tRNA in any amino acid compound; (b) providing a tRNA having an orthogonal relationship to a natural aminoacyl-tRNA synthetase present in a cell-free translation system, and an amino acid compound having the functional group 1, for use as a substrate for the acylation reaction by the ribozyme; (c) performing an aminoacylation of the tRNA with the amino acid compound having the functional group 1 using the ribozyme; (d) providing a tRNA having an orthogonal relationship to a natural aminoacyl-tRNA synthetase present in a cell-free translation system, and an amino acid compound having the functional group 2, for use as a substrate for the acylation reaction by the ribozyme; (e) performing an aminoacylation of the tRNA with the amino acid compound having the functional group 2 using the ribozyme; (f) providing a cell-free translation system containing at least an initiator tRNA, methionine, and a methionyl-tRNA synthetase; (g) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and (h) adding the aminoacylated tRNA obtained in the substep (c), the aminoacylated tRNA obtained in the substep (e), and the template DNA to the cell-free translation system to synthesize the non-cyclic peptide compound;
6. The process of any one of 2-5, wherein the ribozyme capable of catalyzing the aminoacylation reaction of tRNA in any amino acid compound consists of the base sequence (I) or (II) below:

(I)
GGAUCGAAAGAUUUCCGCGGCCCCGAAAGGGGAUUAGCGUUAGGU
(SEQ ID NO: 37)

(II)
GGAUCGAAAGAUUUCCGCAUCCCCGAAAGGGUACAUGGCGUUAGGU
(SEQ ID NO: 38);

7. The process of 1, wherein the pair of functional groups 1 and 2 is one of the following pairs (A) to (C)

[Formula 2]

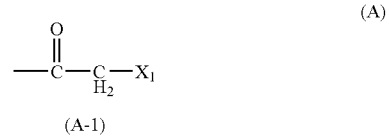

(A-1)

-continued

HS— (A-2)

—C≡C—H (B-1)

N₃— (B-2)

—Ar—CH₂NH₂ (C-1)

[5-hydroxyindole structure] (C-2)

wherein $X_1$ is Cl or Br, and Ar is an aromatic ring optionally having a substituent;

8. The process of 2, wherein the amino acid compound in the substep (b) is a compound of formula (1):

[Formula 3]

[structure: ClH₂C-C(=O)-NH-C(R¹)(R²)-COOCH₂CN] (1)

wherein $R^1$ and $R^2$ represent a hydrogen atom or any substituent connected by carbon; and the amino acid compound in the substep (d) is cysteine;

9. The process of 3, wherein the amino acid compound in the substep (b) is a compound of formula (2), and the amino acid compound in the substep (d) is a compound of formula (3)

[Formula 4]

[structure with H₂NH₂C-, Z₁ substituted benzamide linked to N-C(R¹)(R²)-COOCH₂CN] (2)

[5-hydroxytryptophan OCH₂CN ester structure] (3)

wherein $R^1$ and $R^2$ are as defined above, and $Z_1$ represents any substituent;

10. The process of 4, wherein the amino acid compound in the substep (b) is a compound of formula (4)

[Formula 5]

[structure: chloroacetamido amino acid 3,5-dinitrobenzyl ester with (CH₂)ₘ chain] (4)

wherein m is an integer of 1 to 10; and the amino acid compound in the substep (d) is cysteine;

11. The process of 5, wherein the amino acid compound in the substep (b) is a compound of formula (5), and the amino acid compound in the substep (d) is a compound of formula (6)

[Formula 6]

[structure: azido amino acid 3,5-dinitrobenzyl ester with (CH₂)ₘ chain] (5)

[structure: propargyl amino acid 3,5-dinitrobenzyl ester with (CH₂)ₘ chain] (6)

wherein m is as defined above;

12. The process of 5, wherein the amino acid compound in the substep (b) is a compound of formula (7), and the amino acid compound in the substep (d) is a compound of formula (8)

[Formula 7]

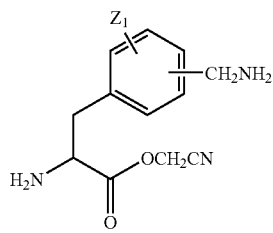
(7)

13. A cyclic peptide compound represented by formula (9) or (10)

[Formula 8]

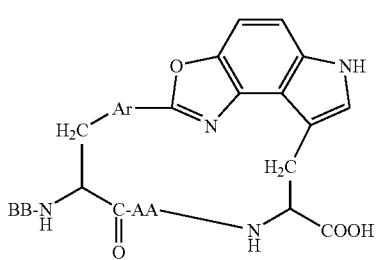
(9)

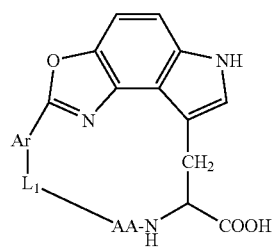
(8)

wherein $Z_1$ is as defined above;

wherein AA represents a peptide chain comprising 2-10 amino acid residues, BB represents a peptide chain comprising one amino acid residue or a peptide chain comprising 2-5 amino acid residues, $L_1$ represents a divalent linking group, and Ar is as defined above;

14. The cyclic peptide compound of 13 represented by formula (11) (SEQ ID NO: 29) or formula (12) (SEQ ID NO: 30)

[Formula 9]

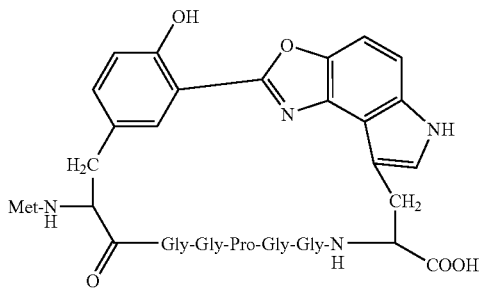
(11)

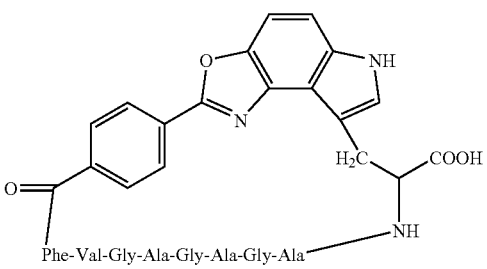
(12)

15. A cyclic peptide compound represented by formula (13)

[Formula 10]

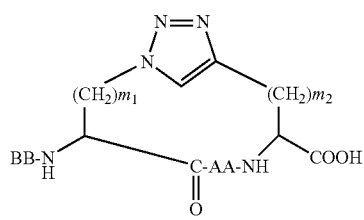
(13)

wherein $m_1$ and $m_2$ independently represent an integer of 1 to 10, and AA and BB are as defined above; and 16. The cyclic peptide compound of 15 represented by formula (14)

[Formula 11]

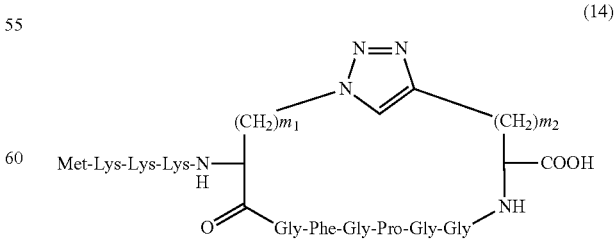
(14)

(SEQ ID NOS: 60 and 61)

wherein $m_1$ and $m_2$ are as defined above.

Advantageous Effect of the Invention

The process of the present invention enables easy and efficient translational synthesis of a cyclic peptide compound. Since the process of the present invention employs translational synthesis to synthesize a non-cyclic peptide compound, it is possible to control sequences thereof by controlling mRNA sequences. This in combination with a display system (mRNA display and ribosomal display) using a cell-free translation system enables prompt screening of functional unique peptides.

BRIEF DESCRIPTION OF THE DRAWINGS

FIG. 7 (SEQ ID NOS: 42 and 31) shows a structure of Urotensin II and a structure of a cyclic peptide compound of formula (35).

EMBODIMENTS

Figure 1:
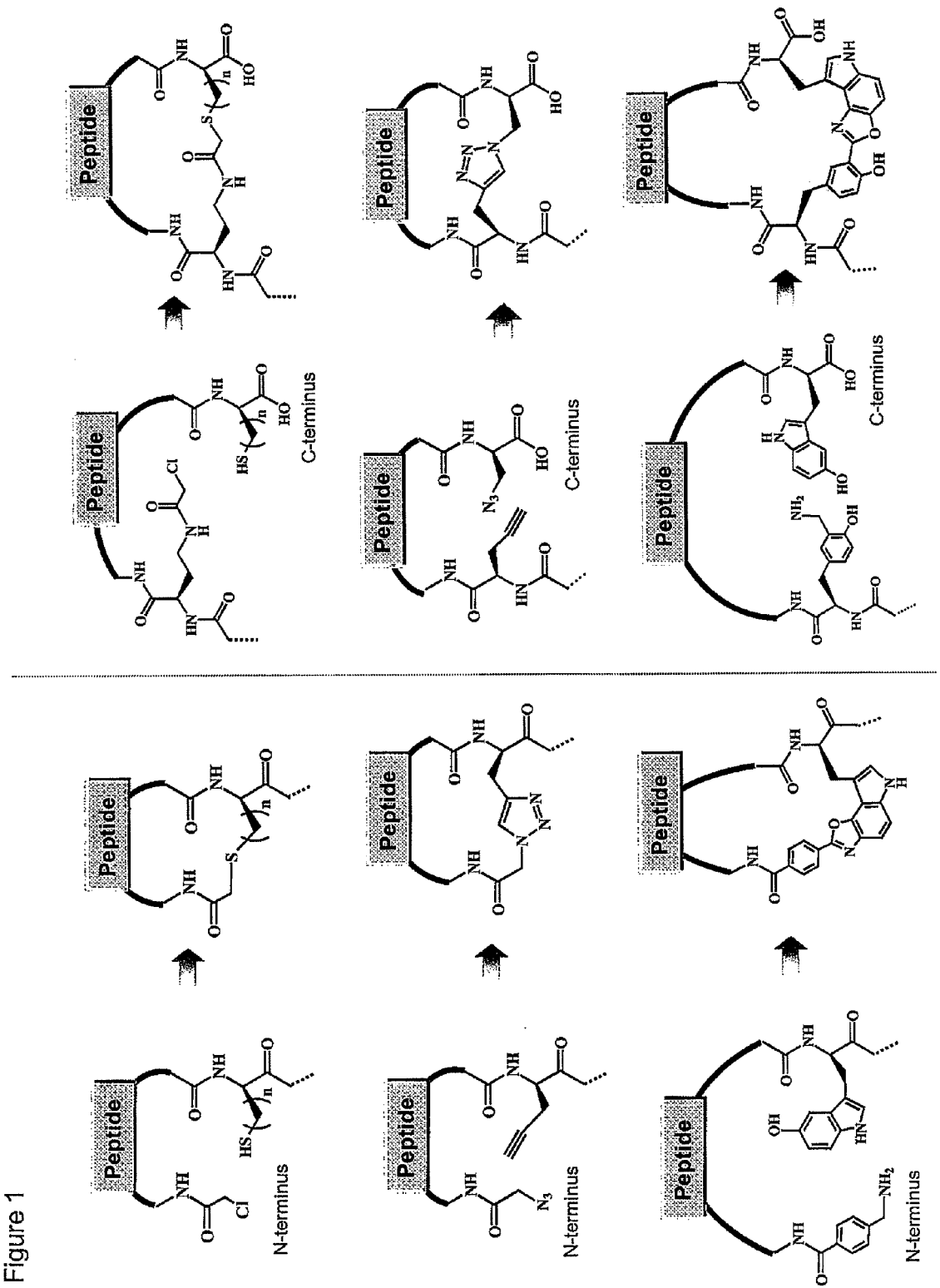
FIG. 1 schematically shows examples of cyclization reactions in the present invention. Forms of cyclization of N-termini and a side chain and forms of cyclization of a side chain of C-termini and a side chain are shown.
Figure 2:
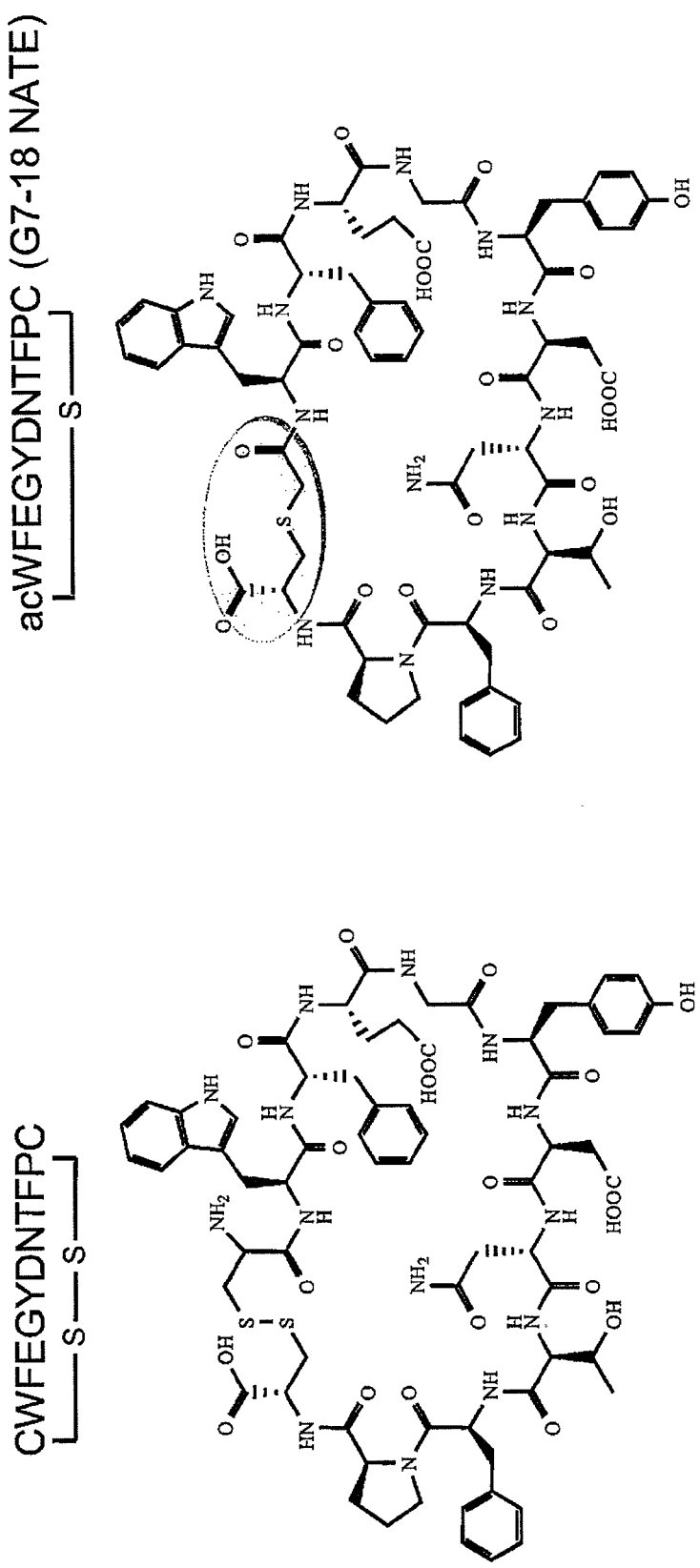
FIG. 2 (SEQ ID NOS: 27 and 28) shows a structure of a cyclic peptide compound of formula (15) and a structure of a cyclic peptide compound of formula (16).
Figure 3:
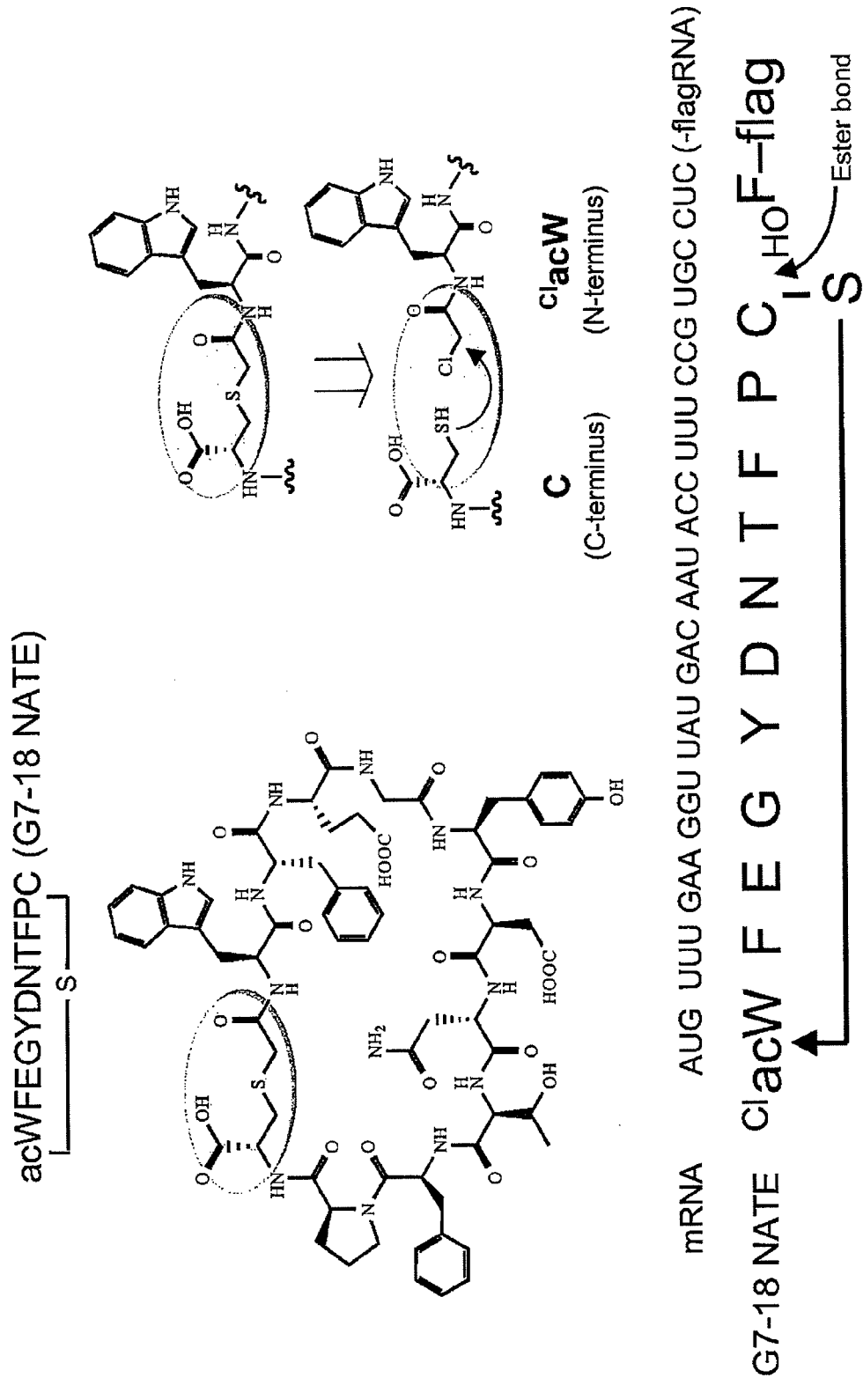
FIG. 3 (SEQ ID NOS: 28 and 39) illustrates a cyclic peptide compound and an mRNA of Example 1-1.

The process for synthesizing a cyclic peptide compound according to the present invention is characterized by comprising translationally synthesizing a non-cyclic peptide compound containing a pair of functional groups (functional group 1 and functional group 2) capable of reacting to form a bond, and thereafter cyclizing the non-cyclic peptide compound by the reaction of the pair of functional groups to form a bond.

As used herein, the term non-cyclic peptide compound includes non-cyclic peptide compounds comprising multiple amino acid compounds connected by peptide bonds, and non-cyclic peptide compounds comprising multiple amino acid compounds that have a part substituted with hydroxycarboxylic acid compounds and are connected by peptide bonds and ester bonds.

As used herein, the term a pair of functional groups (functional group 1 and functional group 2) capable of reacting to form a bond refers to a pair of functional groups, i.e., the functional group 1 and the functional group 2, capable of reacting to form a bond so that a non-cyclic peptide compound is converted into a cyclic peptide compound. Such a pair of functional groups is not particularly limited, as long as the pair of functional groups can react together to form a bond. A type of the reaction of the functional groups is not particularly limited, and various reaction types may be employed such as substitution reaction, addition reaction, condensation reaction, and cyclization addition reaction. Types of bonds (e.g., single bond, double bond, and triple bond) to be formed by the reaction and the number of the bonds are not particularly limited.

An example of the pair of functional groups is a pair of —$CH_2$-L (L represents a leaving group such as —Cl, —Br, and —$OSO_2CH_3$) and a nucleophilic functional group (e.g., —OH, —$NH_2$, and —SH). Specific examples of the pair of functional groups include the following pairs (A) to (C)

[Formula 12]

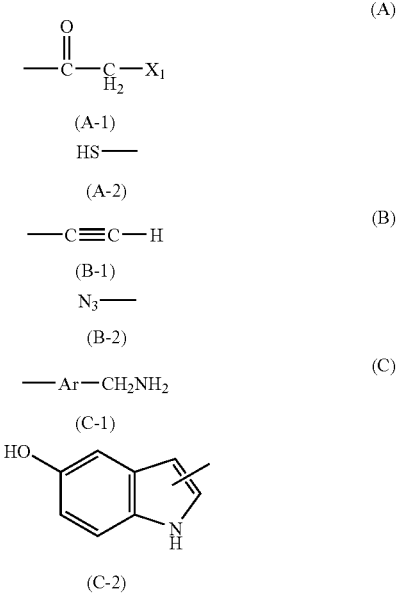

wherein $X_1$ is Cl or Br, and Ar is an aromatic ring optionally having a substituent. The substituent of Ar is not particularly limited, and examples include a hydroxyl group, halogen atom, alkyl group having 1-6 carbon atoms, alkoxy group having 1-6 carbon atoms, phenyl group, phenoxy group, cyano group, and nitro group.

In the case of the pair (A), a structure of formula (A-3) can be obtained by substitution reaction of the functional groups. In the cases (B) and (C), the structures (B-3) and (C-3) can be obtained, respectively, by cyclization reaction of the functional groups.

[Formula 13]

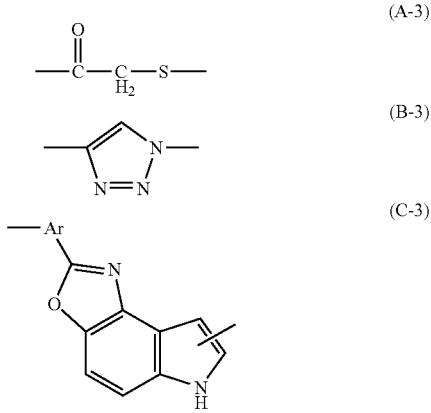

In the present invention, a peptide ring is formed by a bond formation between a pair of functional groups present in a non-cyclic peptide compound. Thus, when an amino acid compound (or hydroxycarboxylic acid compound) constituting the non-cyclic peptide compound is considered as a unit, it is necessary that such a pair of functional groups be present on different amino acid compound (or hydroxycarboxylic acid compound) units. Specifically, the non-cyclic peptide compound synthesized by the translational synthesis has the pair of functional groups on different amino acid compound (or hydroxycarboxylic acid compound) units. It is preferable that at least one amino acid compound unit, e.g., 1-10, 2-10, or 3-5 amino acid compound units, be present between an amino acid compound unit having one of the functional groups and an amino acid compound unit having the other one of the functional groups in the non-cyclic peptide compound.

In the present invention, such a non-cyclic peptide compound having the pair of functional groups is translationally synthesized in a cell-free translation system.

Cell-free polypeptide translational synthesis is to synthesize a polypeptide in vitro in a genetic information translation system formed of a cytoplasmic extract in an artificial container. Cell-free synthesis using no living organism is free from physiological constraints in vivo, and expected to achieve high-throughput polypeptide synthesis from genes and to dramatically enlarge the range of amino acid sequences that can be synthesized. In principle, it is thought that polypeptides consisting of any amino acid sequence can be synthesized in vitro at will only in the presence of genetic information in cell-free polypeptide synthesis systems unless the catalytic function of the translation enzyme system is disturbed. Moreover, non-natural amino acids not occurring in vivo can also be used if they can be successively assigned to genetic information.

Cell-free translation systems that are commonly known are those comprising a ribosomal protein, a ribosomal RNA, an amino acid, tRNA, GTP, ATP, a translation initiation factor, an elongation factor, and other factors necessary for translation, including high-efficiency systems using *E. coli* extracts or wheat germ extracts. These systems produce several hundred micrograms to several milligrams of proteins/mL by continuous supplying energy under dialysis. Some systems contain an RNA polymerase for simultaneous transcription from a gene's DNA. Cell-free translation systems that can be used include *E. coli*-derived systems such as RTS-100® available from Roche Diagnostics and PURESYSTEM® available from PGI, and systems based on wheat germ extracts available from ZOEGENE Corporation.

In cell-free translation systems free from constraints in vivo, peptide compounds consisting of any amino acid sequence can be synthesized at will and at any length in principle. Even unusual amino acids can be used in cell-free translation systems so far as they could be assigned to genetic information. Further, a hydroxycarboxylic acid compound can be used as a part of the amino acids.

In the present invention, for example, translational synthesis of a non-cyclic peptide compound can be performed by the following processes.

Process 1

In one embodiment of the present invention, a non-cyclic peptide compound is translationally synthesized by a process comprising the steps of: (a) providing a ribozyme capable of catalyzing an aminoacylation reaction of a tRNA in any amino acid compound; (b) providing an initiator tRNA and an amino acid compound having the functional group 1 for use as a substrate for the acylation reaction by the ribozyme; (c) performing an aminoacylation of the initiator tRNA with the amino acid compound having the functional group 1 using the ribozyme; (d) providing a cell-free translation system which contains at least an amino acid compound having the functional group 2 and a tRNA to be aminoacylated with the amino acid compound having the functional group 2, and is free of methionine; (e) providing a template DNA for forming an mRNA having at desired positions a codon corresponding to an anticodon of the initiator tRNA, and a codon corresponding to an anticodon of the tRNA to be aminoacylated with the amino acid compound having the functional group 2; and (f) adding the aminoacylated initiator tRNA obtained in the substep (c) and the template DNA to the cell-free translation system to synthesize the non-cyclic peptide compound.

In the non-cyclic peptide compound obtained by the above process, one of the pair of functional groups (functional group 1) is present on an amino acid residue derived from an amino acid compound that binds to the initiator tRNA, and the other one of the functional groups (functional group 2) is present on an amino acid residue incorporated in peptide chain elongation reaction in the cell-free translation system.

In the process, first, the initiator tRNA is aminoacylated with the amino acid compound having the functional group 1 using the ribozyme capable of catalyzing aminoacylation reaction of tRNA in any amino acid compound.

The initiator tRNA in the process is described below.

The initiation of translation of mRNA requires a specific tRNA called initiator tRNA. Translation begins when an aminoacylated initiator tRNA binds to the ribosomal small subunit together with an initiation factor (IF) and the ribosomal small subunit binds to a start codon on mRNA, and the start codon is recognized by the initiator tRNA. The initiator tRNA always carries methionine (formylmethionine in the case of prokaryotic cells) and the methionine codon AUG is normally used as the start codon in nature so that the initiator tRNA has an anticodon corresponding to methionine.

In contrast, the process is characterized in that the initiator amino acid is an amino acid compound having the functional group 1. In other words, it is characterized in that translation is initiated by attaching the amino acid compound having the functional group 1 to the initiator tRNA. In the process, the start codon is not limited to AUG, either. Thus, other codons can also be assigned as start codons. In the process, therefore, the initiator tRNA may have an anticodon corresponding to methionine or may be substituted by another anticodon. For example, the present inventors found that translation can be initiated with even AUA, CGG, CCG, GGC and GCC codons so far as initiator tRNAs having their anticodons were used.

The base sequence of the native initiator tRNA (tRNA^fMet) corresponding to the start codon AUG that can be used in the process is shown below.

5'-GGCGGGGUGGAGCAGCCUG-GUAGCUCGUCGGGCU<u>CAU</u>AACCCGAAG AUCGUCGGUUCAAAUCCGGCCCCCGCAACCA-3' (SEQ ID NO: 1) (the underlined motif represents an anticodon region).

When the start codon is changed, a tRNA having an anticodon complementary to it is used. When a random codon (NNN) is assigned as a start codon, therefore, the sequence of the initiator tRNA is represented as follows.

5'-GGCGGGGUGGAGCAGCCUG-GUAGCUCGUCGGGCU<u>NNN</u>AACCCGAAG AUCGUCGGUUCAAAUCCGGCCCCCGCAACCA-3' (SEQ ID NO: 2) (the underlined motif NNN represents an anticodon consisting of a random nucleotide set). The sequence except for NNN is the body sequence of tRNA^fMet, which is thought to be necessary for attaching the initiation factor.

In the translational synthesis in the process, a start codon corresponding to the anticodon represented by NNN above is present on the mRNA encoding the sequence of the non-cyclic peptide to be translationally synthesized and the start codon encodes a desired initiator amino acid to be placed at the N-terminus of the polypeptide.

Aminoacylation of the initiator tRNA is performed as follows.

Aminoacylation of tRNA is a reaction by which the carboxyl group of an amino acid forms an ester bond with the hydroxyl group at the 3'-end of tRNA (acylated).

In the process, the aminoacylation of the initiator tRNA takes place by using a ribozyme that is an RNA molecule capable of catalyzing tRNA acylation reaction. Ribozymes that can be used in the process are ribozymes having the function of acylating any tRNA with an amino acid compound having a desired structure. Unlike native aminoacylated tRNA synthetases (ARS), such ribozymes do not have specificity to each amino acid compound and each tRNA and allow aminoacylation with any amino acid compound other than the amino acid compound to be charged so that any amino acid compound can be attached to the initiator tRNA.

The ribozymes used in the process can be created by the in vitro molecular evolution described by the present inventors (WO 2007/066627; H. Murakami, H. Saito, and H. Suga (2003) "A versatile tRNA aminoacylation catalyst based on RNA" Chemistry & Biology, Vol. 10, 655-662; and H. Murakami, A. Ohta, H. Ashigai, H. Suga (2006) "The flexizyme system: a highly flexible tRNA aminoacylation tool for the synthesis of nonnatural peptides" Nature Methods 3, 357-359). Unlike native ARS, the ribozymes created by the above process have been evolved to skip the first step of producing a high-energy intermediate (aminoacyl AMP) in aminoacylation reaction and to catalyze only the step of attaching an amino acid compound to tRNA, which requires that a preliminarily modestly activated amino acid should be used as an amino acid compound.

Specific examples of ribozymes that can be used in the present invention include ribozymes consisting of the RNA sequence (I) GGAUCGAAAGAUUUCCGCGGC-CCCGAAAGGGGAUUAGCGUUAGGU (SEQ ID NO: 3) or (II) GGAUCGAAAGAUUUCCGCAUC-CCCGAAAGGGUACAUGGCGUUAGGU (SEQ ID NO: 4), or a variant thereof. The creating of these ribozymes and their precursor flexizyme are described in detail in WO 2007/066627; H. Murakami, A. Ohta, H. Ashigai, H. Suga (2006) "The flexizyme system: a highly flexible tRNA aminoacylation tool for the synthesis of nonnatural peptides" Nature Methods 3, 357-359; and H. Murakami H. Saito, H. Suga (2003) "A versatile tRNA aminoacylation catalyst based on RNA" Chem. Biol. 10, 655-662.

The ribozyme-mediated aminoacylation reaction of the initiator tRNA may be performed in solution or on a column using a ribozyme immobilized on a carrier. When the translation reaction is at a low-volume scale of 100 μL or less for example, the ribozyme-mediated aminoacylation of the initiator tRNA may take place in solution and the pellet precipitated with ethanol from the reaction solution may be dissolved in a suitable buffer (e.g., 1 mM potassium acetate, pH 5) and added to a translation system. Suitable reaction conditions may be chosen as appropriate, but an example of reaction conditions at low-volume scale may involve reacting 0.1 M reaction buffer, pH 7.5 containing (final concentrations) 0.5-20 μM initiator tRNA, 0.5-20 μM ribozyme, 2-10 mM amino acid compound, 0.6 M $MgCl_2$ at 0° C. for 1 hour to 24 hours.

When the translation reaction scale exceeds 100 μL, it is more convenient to use a ribozyme immobilized on a carrier so that the ribozyme may be recycled. Carriers that can be used include, but not limited to, e.g., resins, agarose, Sepharose, magnetic beads, etc. The reaction using a ribozyme immobilized on a carrier can be performed according to the process described in Murakami, H., Bonzagni, N. I. and Suga, H. (2002) "Aminoacyl-tRNA synthesis by a resin-immobilized ribozyme" I. Am. Chem. Soc. 124(24): 6834-6835. The aminoacylated tRNA as the reaction product can be isolated by various processes. As an example, it can be eluted from the column with a buffer containing about 10 mM EDTA. The resin to which the ribozyme is immobilized can be recycled over ten times by equilibration with Reaction Buffer, for example.

As for further details about the ribozyme-mediated aminoacylation reaction, also see the examples herein below.

The amino acid compound having the functional group 1 for use in the process is described below.

As described above, since the amino acid compound having the functional group 1 is incorporated into the initiator tRNA by the ribozyme capable of catalyzing aminoacylation reaction of tRNA in any amino acid compound, various amino acids can be used as long as they have the functional group 1.

Amino acids basically refer to compounds having both amino and carboxyl functional groups in their molecules. Among those, natural amino acids used for normal translation are the following twenty natural amino acids: alanine (Ala, A), valine (Val, V), leucine (Leu, L), isoleucine (Ile, I), proline (Pro, P), tryptophan (Trp, W), phenylalanine (Phe, F), methionine (Met, M), glycine (Gly, G), serine (Ser, S), threonine (Thr, T), tyrosine (Tyr, Y), cysteine (Cys, C), glutamine (Gln, Q), asparagine (Asn, N), lysine (Lys, K), arginine (Arg, R), histidine (His, H), aspartate (Asp, D), and glutamate (Glu, E), which are alpha-aminocarboxylic acids (or substituted alpha-aminocarboxylic acids). As used herein, amino acids include both natural and non-natural amino acids, and these twenty natural amino acids are sometimes specifically called common amino acids.

In contrast to the common amino acids, unusual amino acids refer to amino acids other than the common amino acids, and they may be artificially synthesized or found in nature. Examples of unusual amino acids include beta-amino acids, gamma-amino acids and delta-amino acids containing an additional methylene group in their amino acid structure, and stereoisomers of the common amino acids such as D-amino acids, etc. As used herein, the term amino acid may also include derivatives having a structure in which an amino group or carboxyl group on the amino acid structure has been substituted, and examples of unusual amino acids further include amino acids containing various acyl groups in their amino groups, N-methylated derivatives, statins (beta-hydroxy-gamma-amino acids), pyroglutamic acids, aminobenzenecarboxylic acids etc. In addition, dipeptides, tripeptides or longer peptides are sometimes also expressed as amino acids.

Either of a compound derived from a common amino acid or a compound derived from an unusual amino acid can be used as the amino acid compound having the functional group 1.

As described above, the amino acid compound having the functional group 1 is incorporated into the initiator tRNA by the ribozyme capable of catalyzing aminoacylation reaction of tRNA with any amino acid compound, which requires that a preliminarily modestly activated amino acid compound should be used as described above. In other words, amino acid adenylation is skipped by using an amino acid compound having, at the carbonyl group where acylation proceeds, an ester bond modestly activated by an electron-withdrawing group. Examples of such a modestly activated amino acid compound include esterified compounds such as AMP, cyanomethyl esters, thioesters, and benzyl esters having an electron-withdrawing group such as a nitro group and fluorine. Examples of preferred amino acid compounds include amino acid compounds having a cyanomethyl-esterified, dinitrobenzyl-esterified, or 4-chlorobenzyl-thioesterified carboxyl group, but the present invention is not limited to these examples and those skilled in the art can screen suitable leaving groups having a high reaction efficiency to use them, and the use of an amino acid compound having such a suitable leaving group is also naturally included in the scope of the present invention.

When the ribozyme (I) or (II) or a variant thereof is used as a ribozyme, their amino acid compounds must have an aromatic ring in their amino acid side chain or leaving group so that they can be recognized by the ribozyme. For example, in the case of cyanomethyl-esterified alpha-amino acid, it is necessary that the amino acid be an alpha-amino acid having an aromatic ring at a substituent on the alpha-carbon as shown in formula (17) below, or an alpha-amino acid having an aromatic ring in an ester group that is to be eliminated at the time of acylation as shown in formula (18) below.

[Formula 14]

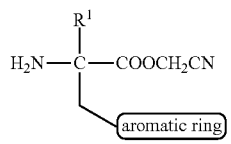
(17)

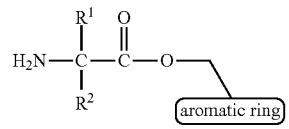
(18)

The amino acid of formula (17) can be synthesized by, for example, process described in JPA 2005-528090 and Suga et al., J. Am. Chem. Soc., 120, 1151-1156, 1998.

The amino acid of formula (18) can be synthesized by, for example, reacting an amino acid having a Boc-protected amino group with a halomethyl aromatic compound having an electron-withdrawing group on an aromatic ring (e.g., benzyl bromide having an electron-withdrawing group) to esterify the amino acid, and then eliminating the Boc protection group by use of an acid. Alternatively, the amino acid of formula (18) can be synthesized by condensing an amino acid having a Boc-protected amino group and a hydroxymethyl aromatic compound having an electron-withdrawing group (e.g., benzyl alcohol having an electron-withdrawing group) or an aromatic methylthiol compound having an electron-withdrawing group (e.g., benzyl mercaptan) by use of a common condensing agent (e.g., dicyclohexylcarbodiimide).

The functional group 1 of the amino acid compound may be present as a substituent on a carbon atom of the amino acid, such as alpha-carbon and beta-carbon, or may be present on a substituent on these carbon atoms. The functional group 1 of the amino acid compound may be present as a substituent on a nitrogen atom of an amino group, or may be present on a substituent on the nitrogen atom of the amino group. It is necessary that the functional group 1 can react with the functional group 2 of the amino acid compound of the step (d) to form a bond. As described below, the amino acid compound of the step (d) is a common amino acid, and the functional group 2 is basically a nucleophilic functional group (e.g., —SH, —COOH, and —OH) contained in cysteine, tyrosine, and the like; thus, it is preferable that the functional group 1 is a functional group having an appropriate leaving group, such as —CH$_2$-L (L represents a leaving group, such as —Cl, —Br, and —OSO$_2$CH$_3$).

Specifically, amino acid compounds having the above group (A-1) on a nitrogen atom of an amino group are preferred. Specific examples of amino acid compounds include the compound of formula (1) shown above. In formula (1), R$^1$ and R$^2$ represent a hydrogen atom or any substituent connected by carbon to a carbon atom at the alpha position. Specifically, it is preferable that R$^1$ and R$^2$ be, for example, substituents on alpha-carbon atoms of the above 20 natural amino acids (common amino acids). It is preferable that R$^1$ and R$^2$ be a pair of substituents on alpha-carbon atoms of the common amino acids. A compound of formula (19)

[Formula 15]

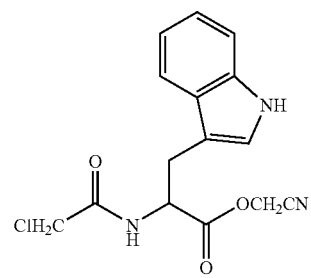
(19)

is a specific example of the compound of formula (1).

The cell-free translation system of the process is described below.

It is necessary that the cell-free translation system be free of methionine so that translation is initiated with the initiator tRNA aminoacylated with the amino acid compound having the functional group 1. The cell-free translation system may be free of methionine and methionyl-tRNA synthetase.

It is necessary that the cell-free translation system contain the amino acid compound having the functional group 2 and a tRNA to be aminoacylated with the amino acid compound having the functional group 2. The amino acid compound having the functional group 2 is basically a common amino acid, and examples include cysteine, aspartate, glutamine, and tyrosine. In other words, the functional group 2 is —OH, —SH, —C(=O)NH$_2$, —COOH, or the like. It is preferable that the amino acid compound having the functional group 2 be cysteine.

The cell-free translation system contains, in addition to those described above, other factors necessary for translation, such as amino acids necessary for peptide chain elongation and tRNAs. Any common amino acid, unusual amino acids obtained through reprogramming of a genetic code, and hydroxycarboxylic acid compounds (e.g., lactic acid and phenyllactic acid) can be used as the amino acids necessary for peptide chain elongation.

The template DNA for forming an mRNA in the process is described below.

The mRNA in the process has at desired positions a codon corresponding to an anticodon of the initiator tRNA and a codon corresponding to an anticodon of the tRNA to be aminacylated with the amino acid compound having the functional group 2. Since reaction of the functional group 1 with the functional group 2 is necessary, it is preferable that the amino acid compounds having the functional groups 1 and 2 be positioned in the non-cyclic peptide compound such that at least one amino acid compound unit is present between the amino acid compounds. Thus, it is preferable that the two codons in the mRNA be positioned such that 1-20, 2-10, or 3-5 codons are present between the two codons. Such an mRNA is created in the cell-free translation system by adding to the system a template DNA designed appropriately to form such an mRNA.

Such a template DNA is prepared on the basis of a structure of a non-cyclic peptide compound that is to be synthesized. Any known method can be employed to prepare the template DNA. The amino acids necessary for peptide chain elongation, tRNAs, and the like to be contained in the cell-free translation system are determined on the basis of the structure of the non-cyclic peptide compound that is to be synthesized.

Then, the initiator tRNA aminoacylated with the amino acid compound having the functional group 1 and the template DNA are added to the cell-free translation system to synthesize a non-cyclic peptide compound.

Process 2

In one embodiment of the present invention, a non-cyclic peptide compound is translationally synthesized by a process comprising the steps of: (a) providing a ribozyme capable of catalyzing an aminoacylation reaction of a tRNA with any amino acid compound; (b) providing an initiator tRNA and an amino acid compound having the functional group 1 for use as a substrate for the acylation reaction by the ribozyme; (c) performing an aminoacylation of the initiator tRNA with the amino acid compound having the functional group 1 using the ribozyme; (d) providing a tRNA having an orthogonal relationship to a natural aminoacyl-tRNA synthetase present in a cell-free translation system, and an amino acid compound having the functional group 2, for use as a substrate for the acylation reaction by the ribozyme; (e) performing an aminoacylation of the tRNA with the amino acid compound having the functional group 2 using the ribozyme; (f) providing a cell-free translation system free of methionine; (g) providing a template DNA for forming an mRNA having at desired positions a codon corresponding to an anticodon of the initiator tRNA, and a codon corresponding to an anticodon of the tRNA; and (h) adding the aminoacylated initiator tRNA obtained in the substep (c), the tRNA aminoacylated in the substep (e) with the amino acid compound having the functional group 2, and the template DNA to the cell-free translation system to synthesize the non-cyclic peptide compound.

In the non-cyclic peptide compound obtained by the process, the functional group 1 is present at an amino acid residue derived from an amino acid compound that binds to the initiator tRNA, and the functional group 2 is present on an amino acid residue that is incorporated in peptide chain elongation reaction.

The ribozyme capable of catalyzing an aminoacylation reaction of a tRNA with any amino acid compound, the initiator tRNA, the aminoacylation of the initiator tRNA with the amino acid compound having the functional group 1, and the like are the same as those in Process 1.

In the process, aminoacylation of the tRNA having the orthogonal relationship to the natural aminoacyl-tRNA synthetase (ARS) present in the cell-free translation system is performed using the ribozyme capable of catalyzing the aminoacylation reaction of the tRNA with any amino acid compound and the amino acid compound having the functional group 2, and thereafter the aminoacylated tRNA is applied to the cell-free translation system. When a tRNA that does not have the orthogonal relationship to ARS is used, there is a possibility that ARS present in the cell-free translation system causes the tRNA to be aminoacylated with another amino acid to incorporate this amino acid instead of the amino acid compound having the functional group 2. Thus, the tRNA having the orthogonal relationship to ARS are used.

The tRNA having the orthogonal relationship to natural ARS is a suppressor tRNA that is not aminoacylated with natural ARS present in a translation system and is capable of efficiently suppressing a codon at a mutation site in a ribosome to express a desired unusual amino acid or carboxylic acid. Examples of such tRNAs that can be used include natural amber suppressor tRNAs derived from different species, and artificially constructed tRNAs. An example of artificially constructed tRNAs is an otRNA (orthogonal tRNA). This is an artificial tRNA derived from an *E. coli* amber suppressor tRNA$^{Asn}_{CUA}$ and having a G73A mutant. Some parts of the otRNA are artificially modified so that the otRNA is not recognized by *E. coli* ARS; therefore, the otRNA is not aminoacylated in an *E. coli* translation system. An amber suppressor tRNA derived from a species (e.g., human) different from an extracellular translation system can be used as a naturally derived tRNA-like molecule for the foregoing purpose.

As in Process 1, it is necessary that the cell-free translation system of the process be free of methionine and methionyl-tRNA synthetase. As in Process 1, the cell-free translation system contains amino acids necessary for peptide chain elongation, tRNAs, and other factors necessary for translation.

The template DNA for forming the mRNA of the process is described below.

The mRNA in the process has at desired positions a codon corresponding to an anticodon of the initiator tRNA and a codon corresponding to an anticodon of the tRNA having the orthogonal relationship. It is preferable that these codons be positioned such that, for example, 1-20, 2-10, or 3-5 codons are present between the codons. Such an mRNA is created in the cell-free translation system by adding to the system a template DNA designed appropriately to form such an mRNA. Such a template DNA is prepared on the basis of a structure of a non-cyclic peptide compound that is to be synthesized. Any known method can be employed to prepare the template DNA. The amino acids necessary for peptide chain elongation, tRNAs, and the like to be contained in the cell-free translation system are determined on the basis of the structure of the non-cyclic peptide compound that is to be synthesized.

As described above, it is necessary that the amino acid compound having the functional group 1 and the amino acid compound having the functional group 2 be preliminarily modestly activated.

The amino acid compound having the functional group 1 and the amino acid compound having the functional group 2 are not particularly limited, as long as they have the functional group 1 and the functional group 2, respectively. The functional group 1 and the functional group 2 can be present at a substituent on a nitrogen atom of an amino group, or at a substituent on a carbon atom such as alpha-carbon and beta-carbon.

To have the functional groups on the nitrogen atom, the functional groups may be incorporated onto a nitrogen atom of an amino group of an amino acid as an acyl substituent or as a part of the acyl substituent as shown in, for example, formula (20) to formula (24)

[Formula 16]

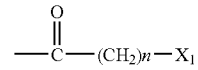  (20)

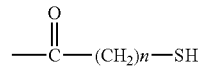  (21)

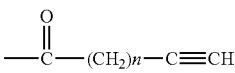  (22)

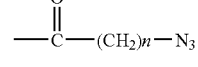  (23)

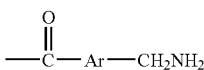  (24)

wherein n is an integer of 1 or greater, e.g., an integer of 1 to 10, and $X_1$ is as defined above.

To have the functional groups on the carbon atoms such as alpha-carbon and beta-carbon, the functional groups may be incorporated as groups shown in, for example, formula (25) to formula (30)

[Formula 17]

  (25)

  (26)

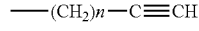  (27)

  (28)

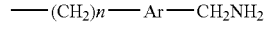  (29)

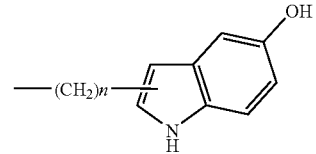  (30)

wherein n is an integer of 1 or greater, e.g., an integer of 1 to 10, and $X_1$ is as defined above.

A specific example of the amino acid compound having the functional group 1 is the compound of formula (2). A specific example of the amino acid compound having the functional group 2 is a compound of formula (3). In formula (2), $R^1$ and $R^2$ are as defined above, and $Z_1$ represents any substituent. Examples of $Z_1$ include a hydroxyl group, halogen atom, alkyl group having 1-6 carbon atoms, alkoxy group having 1-6 carbon atoms, phenyl group, phenoxy group, cyano group, and nitro group. A compound of formula (31)

[Formula 18]

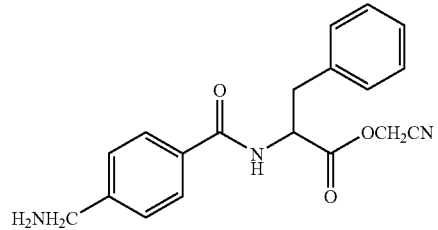  (31)

is a specific example of the compound of formula (2).

Process 3

In one embodiment of the present invention, a non-cyclic peptide compound is translationally synthesized by a process comprising the steps of: (a) providing a ribozyme capable of catalyzing an aminoacylation reaction of a tRNA with any amino acid compound; (b) providing a tRNA having an orthogonal relationship to a natural aminoacyl-tRNA synthetase present in a cell-free translation system, and an amino acid compound having the functional group 1, for use as a substrate for the acylation reaction by the ribozyme; (c) performing an aminoacylation of the tRNA with the amino acid compound having the functional group 1 using the ribozyme; (d) providing a cell-free translation system containing at least an amino acid compound having the functional group 2, a tRNA to be aminoacylated with the amino acid compound having the functional group 2, an initiator tRNA, methionine, and a methionyl-tRNA synthetase; (e) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and (f) adding the aminoacylated tRNA obtained in the substep (c) and the template DNA to the cell-free translation system to synthesize the non-cyclic peptide compound.

In the non-cyclic peptide compound obtained by the process, the functional groups 1 and 2 are present on amino acid residues incorporated in peptide chain elongation reaction.

In the process, translation is initiated with the initiator tRNA that is to be aminoacylated with methionine contained in the cell-free translation system. An initiator tRNA having an anticodon corresponding to methionine is used.

The ribozyme capable of catalyzing the aminoacylation reaction of the tRNA in any amino acid compound, the tRNA having the orthogonal relationship to the natural aminoacyl-tRNA synthetase present in the cell-free translation system, and the aminoacylation with the amino acid compound having the functional group 1 are the same as those in the processes described above.

The cell-free translation system in the process contains at least the amino acid compound having the functional group 2, the tRNA to be aminoacylated with the amino acid compound having the functional group 2, the initiator tRNA, methionine, and the methionyl-tRNA synthetase.

As described above, it is necessary that the amino acid compound having the functional group 1 be preliminarily modestly activated.

As in Process 1, the amino acid compound of the step (d) is a common amino acid, and the functional group 2 is basically a nucleophilic functional group (e.g., —SH, —COOH, and —OH) contained in cysteine, tyrosine, and the like; thus, it is preferable that the functional group 1 of the amino acid compound of the step (b) is a functional group having an appropriate leaving group, such as —CH$_2$-L (L represents a leaving group, such as —Cl, —Br, and —OSO$_2$CH$_3$).

A specific example of the amino acid compound having the functional group 1 is the compound of formula (4). It is preferable that the amino acid compound having the functional group 2 be cysteine.

In formula (4), m represents an integer of 1 to 10. A specific example of the compound of formula (4) is a compound of formula (4) wherein m is 2, and this compound can be produced from, for example, 2,4-diaminobutyric acid.

It is necessary that the cell-free translation system of the process contain methionine and a methionyl-tRNA synthetase. As in the processes described above, the cell-free translation system contains other factors necessary for translation, such as amino acids necessary for peptide chain elongation and tRNAs.

As in the processes described above, the template DNA of the process is a DNA capable of forming an mRNA having at desired positions (e.g., 1-20 codons are present between the following codons) a codon corresponding to an anticodon of the tRNA to be aminoacylated with the amino acid compound having the functional group 1, and a codon corresponding to an anticodon of the tRNA to be aminoacylated with the amino acid compound having the functional group 2.

Process 4

In one embodiment of the present invention, a non-cyclic peptide compound is translationally synthesized by a process comprising the steps of: (a) providing a ribozyme capable of catalyzing an aminoacylation reaction of a tRNA in any amino acid compound; (b) providing a tRNA having an orthogonal relationship to a natural aminoacyl-tRNA synthetase present in a cell-free translation system, and an amino acid compound having the functional group 1, for use as a substrate for the acylation reaction by the ribozyme; (c) performing an aminoacylation of the tRNA with the amino acid compound having the functional group 1 using the ribozyme; (d) providing a tRNA having an orthogonal relationship to a natural aminoacyl-tRNA synthetase present in a cell-free translation system, and an amino acid compound having the functional group 2, for use as a substrate for the acylation reaction by the ribozyme; (e) performing an aminoacylation of the tRNA with the amino acid compound having the functional group 2 using the ribozyme; (f) providing a cell-free translation system containing at least an initiator tRNA, methionine, and a methionyl-tRNA synthetase; (g) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and (h) adding the aminoacylated tRNA obtained in the substep (c), the aminoacylated tRNA obtained in the substep (e), and the template DNA to the cell-free translation system to synthesize the non-cyclic peptide compound.

The functional group 1 and the functional group 2 in the non-cyclic peptide compound obtained by the process are present on amino acid residues incorporated by peptide chain elongation reaction.

In the process, translation is initiated with the initiator tRNA that is to be aminoacylated with methionine contained in the cell-free translation system. An initiator tRNA having an anticodon corresponding to methionine is used.

The ribozyme capable of catalyzing the aminoacylation reaction of the tRNA with any amino acid compound, the tRNA having the orthogonal relationship to the natural aminoacyl-tRNA synthetase present in the cell-free translation system, and the aminoacylation with the amino acid compound having the functional group 1 or 2 are the same as those in the processes described above.

As described above, it is necessary that the amino acid compound having the functional group 1 and the amino acid compound having the functional group 2 be preliminarily modestly activated.

The amino acid compound having the functional group 1 and the amino acid compound having the functional group 2 are not particularly limited, as long as they have the functional group 1 and the functional group 2, respectively. The functional group 1 and the functional group 2 can be present at a substituent on a nitrogen atom of an amino group, or at a substituent on a carbon atom such as alpha-carbon and beta-carbon. It is preferable that the functional groups 1 and 2 be present at a substituent on a carbon atom such as alpha-carbon and beta-carbon. Examples of the functional groups 1 and 2 include those specified in Process 2 as examples.

Specific examples of the amino acid compound having the functional group 1 include compounds of formulas (5) and (7) shown above. In formulas (5) and (7), $Z_1$ and m are as defined above. A compound of formula (32)

[Formula 19]

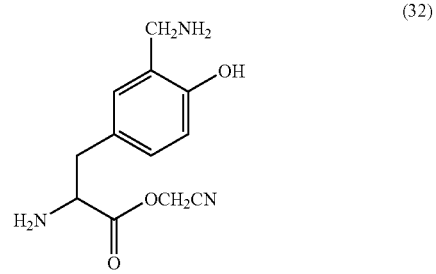

is a specific example of the compound of formula (7).

Specific examples of the amino acid compound having the functional group 2 include the compounds of formulas (6) and (8) shown above. In formula (6), m is as defined above.

Examples also include a pair of a compound having the functional group (A-1) (e.g., compound of formula (4)) as the amino acid compound having the functional group 1 and an unusual amino acid compound having a —SH group, such as homocysteine and mercaptonorvaline, as the amino acid compound having the functional group 2.

It is necessary that the cell-free translation system of the process contain methionine and a methionyl-tRNA synthetase. As in the processes described above, the cell-free translation system contains other factors necessary for translation, such as amino acids necessary for peptide chain elongation and tRNAs.

As in Process 3, the template DNA of the process is a DNA capable of forming the mRNA having the two codons at desired positions (e.g., 1-20 codons are present between the two codons).

Cyclization of Non-Cyclic Peptide Compound

The non-cyclic peptide compound synthesized as described above is then cyclized to synthesize a cyclic peptide compound.

Cyclization of the non-cyclic peptide compound is performed by selecting appropriate reaction conditions according to a type of the pair of functional groups (functional group 1 and functional group 2) present in the non-cyclic peptide compound and capable of reacting to form a bond.

Cyclization of the non-cyclic peptide compound can be performed by isolating the non-cyclic peptide compound and then leaving the non-cyclic peptide compound under appropriate reaction conditions, or by adjusting the cell-free translation system to appropriate reaction conditions without isolation of the non-cyclic peptide compound. Some types of the pair of functional groups cyclize under conditions of the cell-free translation system for synthesizing the non-cyclic peptide compound; in this case, a cyclic peptide compound can be obtained without any special adjustment of reaction conditions.

Examples of reaction conditions for cyclizing the non-cyclic peptide compound are as follows; in the case in which the pair of functional groups is a pair of —$CH_2$-L (L represents a leaving group, such as —Cl and —Br) and —SH, which is a nucleophilic functional group, the non-cyclic peptide compound can be cyclized by isolating the non-cyclic peptide compound and thereafter heating the isolated compound in an appropriate solvent (e.g., 40-100° C.), or by maintaining the cell-free translation system at 35-40° C. for several hours (e.g., at 37° C. for 3 hours) without isolation of the non-cyclic peptide compound.

In the case in which the pair of functional groups is the pair (A), the non-cyclic peptide compound can be cyclized by, for example, isolating the non-cyclic peptide compound and thereafter heating the isolated compound in an appropriate solvent (e.g., 40-100° C.), or by maintaining the cell-free translation system at, for example, 35-40° C. for several hours (e.g., at 37° C. for 3 hours) without isolation of the non-cyclic peptide compound. In the case in which the pair of functional groups is the pair (A), since the functional groups (A-1) and (A-2) have relatively high reactivity, reaction of the functional groups may proceed in some cases in the cell-free translation system for the synthesis of the non-cyclic peptide compound to result in isolation of a cyclic peptide compound from the cell-free translation system (refer to Examples 1-3 below).

In the case in which the pair of functional groups is the pair (B), the non-cyclic peptide compound isolated from the cell-free translation system can be cyclized (Huisgen cyclization) by treating the compound with a monovalent copper salt (produced by reducing copper(II) sulfate with ascorbate in the system) in an appropriate solvent to have the structure (B-3).

In the case in which the pair of functional groups is the pair (C), the non-cyclic peptide compound is isolated and then treated with potassium ferricyanide ($K_3[Fe(CN)_6]$) in an appropriate solvent so that the non-cyclic peptide compound can react to have the structure (C-3).

Cyclic Peptide Compound

The present invention further relates to cyclic peptide compounds represented by formula (9) or (10) shown above. These compounds can be obtained by synthesizing a non-cyclic peptide compound having the functional groups (C-1) and (C-2) by the foregoing processes and then treating the non-cyclic peptide compound with $K_3[Fe(CN)_6]$ to cause reaction.

In formulas (9) and (10), AA represents a peptide chain comprising 2-10 amino acid residues, BB represents a peptide chain comprising one amino acid residue or a peptide chain comprising 2-5 amino acid residues, $L_1$ represents a divalent linking group, and Ar is as defined above. AA and BB are derived from amino acid compounds that are used in the synthesis of the non-cyclic peptide compound. AA and BB are not particularly limited, as long as they are amino acid compounds that can be used in the synthesis. Examples of $L_1$ include linking groups such as an alkylene group (e.g., methylene group), —C(=O)—, and —C(=O)—NH—.

It is known that the ring structure (C-3) of these compounds is a structure that emits fluorescent light when illuminated with excitation light. Thus, the cyclic peptide compounds of the present invention also emit fluorescent light when illuminated with excitation light. Therefore, it may be possible to use the cyclic peptide compounds of the present invention in analysis and detection processes using fluorescence emission.

A specific example of the cyclic peptide compound of formula (9) is a compound of formula (11) shown above, and a specific example of the cyclic peptide compound of formula (10) is a compound of formula (12) shown above. For details of the synthesis of these compounds, refer to Examples 5-1 and 5-2 below.

The present invention further relates to a cyclic peptide compound represented by formula (13) shown above. This compound can be obtained by synthesizing a non-cyclic peptide compound having the functional groups (B-1) and (B-2) by the processes described above and then treating the non-cyclic peptide compound with a monovalent copper salt (produced in the system) to cause reaction. A specific example of the cyclic peptide compound of formula (13) is a compound of formula (14) shown above, e.g., a compound of formula (14) wherein $m_1$ represents 4 and $m_2$ represents 1. For details of the synthesis of the compound, refer to Example 4 below.

The cyclic peptide compound of the present invention is considered to have various in vivo physiological actions. Thus, it is considered that the cyclic peptide compound of the present invention is useful as a bioactive substance, such as pharmaceuticals, or as a reference substance for use in evaluation of bioactive substances.

The following examples further describe the present invention, but should not be construed to limit the scope of the present invention.

Examples

In the examples described below, the ribozyme (I) or ribozyme (II) was used as an ARS ribozyme, and a prokaryotic-derived reconstructed cell-free synthesis system comprising a transcription system from cDNA was used as a translation system.

1. Synthesis of Amino Acid Substrates

The present example describes the synthesis of amino acid substrates (hereinafter sometimes simply referred to as "substrates") having modestly activated ester bonds for use as substrates for acylation reaction mediated by the ribozyme (I) or (II).

1.1 Amino Acids having no Aromatic Ring in their Side Chain (Activated with DBE)

A typical procedure for synthesizing substrates consisting of the title amino acids containing DBE is explained for $^{Cl}$B-DBE (formula (33)) as an example. To 0.1 ml of dimethylformamide were added alpha-N-Boc-ClAcDab-OH (formula (34)) (35.3 mg, 0.12 mmol), triethylamine (21 mg, 0.21 mmol), and 3,5-dinitrobenzyl chloride (45.5 mg, 0.21 mmol) and mixed, and the mixture was stirred at room temperature for 12 hours. After the reaction was completed, diethyl ether (3 ml) was added, and the solution was washed with 0.5 M HCl (5 mL×3), 4% NaHCO$_3$ (5 mL×3), and brine (5 mL×x1) and dried over magnesium sulfate to remove water in the organic layers, and then the solvent was distilled off under reduced pressure. The crude residue was dissolved in 4M hydrochloric acid/ethyl acetate (1 ml), and the solution was allowed to stand at room temperature for 20 minutes. After the reaction was completed, dichloromethane (3 mL) was added and the solvent was distilled off under reduced pressure three times to remove excessive HCl. Diethyl ether (3 mL) was added to form a precipitate, which was recovered by filtration to give $^{Cl}$B-DBE at a total yield of 39% (19 mg, 0.046 mmol).

$^1$H NMR (DMSO-d6, 500 MHz) δ 8.88 (s, 1H), 8.74 (s, 2H), 8.42 (br, 3H), 8.30 (br, 1H), 5.49 (m, 2H), 4.18 (m, 1H), 4.05 (s, 2H), 3.26 (m, 2H), 2.02 (m, 1H), 1.94 (m, 1H)

[Formula 20]

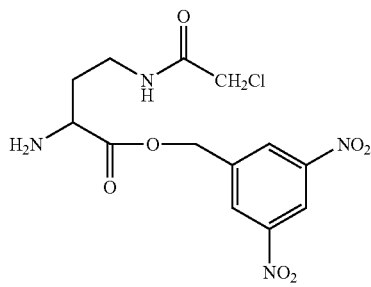

(33)

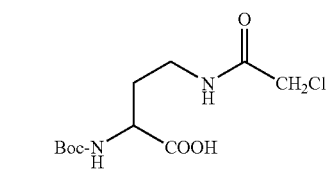

(34)

1.2 Amino Acids having an Aromatic Ring in their Side Chain (Activated with CME)

A typical procedure for synthesizing substrates consisting of the title amino acids containing CME (cyanomethyl ester) is explained for W$^{OH}$-CME (compound of formula (3)) as an example.

Alpha-N-Boc-L-5-hydroxytryptophan (90 mg, 0.28 mmol), triethylamine (40.0 mg, 0.336 mmol), and chloroacetonitrile (358 mg, 4.8 mmol) were mixed, and the mixture was stirred at room temperature for 5 hours. After the reaction was completed, the solvent was distilled off under reduced pressure, and ethyl acetate (3 ml) was added. The solution was washed with 1N HCl (3 mL×3), 1N NaHCO$_3$ (3 mL×3), and brine (3 mL×1) and dried over magnesium sulfate to remove water in the organic layers, and then the solvent was distilled off under reduced pressure. The crude residue was dissolved in 4M hydrochloric acid/ethyl acetate (3 ml), and the solution was allowed to stand at room temperature for 20 minutes. After the reaction was completed, diethyl ether (3 mL) was added, and the solvent was distilled off under reduced pressure three times to remove excessive HCl. Diethyl ether (3 mL) was added to form a precipitate, and W$^{OH}$-CME was obtained at a total yield of 62% (45.1 mg, 0.174 mmol).

$^1$H NMR (DMSO-d6, 500 MHz) δ 10.80 (s, 1H), 8.72 (br, OH), 8.47 (s, 2H), 7.19 (d, J=8.6 Hz, 1H), 7.11 (s, 1H), 6.81 (s, 1H), 6.48 (d, J=8.6 Hz, 1H), 5.10 (s, 2H), 4.34 (m, 1H), (d, J=6.43, 2H)

1.3 N-acylated Amino Acids

A typical procedure for synthesizing N-acylated amino acid substrates containing CME (N-acyl-aminoacyl-CME) is explained for $^{ba}$F-CME (compound of formula (31)) as an example.

Phenylalanine (82.5 mg, 0.50 mmol), [p-(N-Boc-aminomethyl)benzoyl]-N-hydroxysuccinimide (209.0 mg, 0.60 mmol), and NaHCO$_3$ (100 mg, 1.2 mmol) were added to a 50% aqueous dioxane solution (1.2 mL) and mixed, and the mixture was stirred at room temperature for 1 hour. After the reaction was completed, the solvent was distilled off under reduced pressure to remove dioxane, and the solution was washed with ethyl acetate (3 mL×2). The aqueous layer was acidified with 1M HCl, and the solution was extracted with ethyl acetate (3 mL×2) and dried over magnesium sulfate to remove water in the organic layers, and then the solvent was distilled off under reduced pressure (183.4 mg, 0.42 mmol). Then, introduction of CME and removal of Boc were performed by the process described in 1.2 above to obtain $^{ba}$F-CME at a total yield of 81% (153.3 mg, 0.41 mmol).

$^1$H NMR (DMSO-d6, 500 MHz) δ 9.05 (m, 1H), 8.44 (br, 3H), 7.83 (t, J=8.1 Hz, 1H), 7.55 (t, J=8.0 Hz, 1H), 7.34-7.26 (m, 4H), 7.20 (t, J=7.1 Hz, 1H), 5.03-4.49 (m, 2H), 4.08 (s, 2H), 3.22-3.11 (m, 2H).

N-{3-[4-(aminomethyl)phenyl]propanoyl}phenylalanine cyanomethyl ester ($^{bza}$F-CME) was synthesized as follows. Phenylalanine (21 mg, 0.13 mmol), N-{3-[4-(N-Boc-aminomethyl)phenyl]propanoyl}succinimide (45 mg, 0.12 mmol), 1M NaHCO$_3$ aqueous solution (130 μL, 0.13 mmol), water (370 μL), and dioxane (500 μL) were mixed, and the mixture was stirred at room temperature for 3 hours. After the reaction was completed, the solvent was distilled off under reduced pressure to remove dioxane, and the solution was washed with ethyl acetate (1 mL×3). The aqueous layer was acidified with 1M HCl, and the solution was extracted with ethyl acetate (1 mL×3) and dried over magnesium sulfate to remove water in the organic layers, and the solvent was distilled off under reduced pressure. Then, introduction of CME and removal of Boc were performed by the process described in 1.2 above to obtain N-{3-[4-(aminomethyl)phenyl]propanoyl}phenylalanine cyanomethyl ester ($^{bza}$F-CME) (17 mg, 40%).

¹H NMR (DMSO-d₆, 500 MHz): δ 8.53 (s, 1H), 8.19 (br, 1H), 7.33 (d, J=7.9 Hz, 2H), 7.30-7.21 (m, 5H), 7.19 (d, J=7.9 Hz, 2H), 4.97 (s, 2H), 4.51 (m, 1H), 3.99 (s, 2H), 3.05 (q, J=13.8, 5.6 Hz, 2H), 2.93 (q, J=13.7, 9.4 Hz, 2H), 2.75 (t, J=7.5, 2H), 2.38 (t, J=7.5, 2H).

¹³C NMR (DMSO-d₆, 125 MHz): δ 171.8, 171.0, 141.8, 137.0, 131.8, 129.3, 129.0, 128.6, 128.5, 126.9, 115.9, 53.7, 49.6, 42.2, 36.5, 30.6. HRMS (FAB) calculated for $C_{21}H_{31}N_3O_3$ ([M+H]⁺) 366.1818. found 366.1838.

2. Synthesis of RNA

All of the oligonucleotides were purchased from Operon Biotechnologies (Japan). tRNA$^{fMet}_{CAU}$ was synthesized by in vitro transcription from template DNAs amplified with the following primers.

```
P1:
                                       (SEQ ID NO: 5)
5'-GTAAT ACGAC TCACT ATAGG CGGGG TGGAG CAGCC TGGTA

GCTCG TCGG-3'

P2:
                                       (SEQ ID NO: 6)
5'-GAACC GACGA TCTTC GGGTT ATGAG CCCGA CGAGC TACCA

GGCT-3'

P3:
                                       (SEQ ID NO: 7)
5'-GCATA TGTAA TACGA CTCAC TATAG-3'

P4:
                                       (SEQ ID NO: 8)
5'-TGGTT GCGGG GGCCG GATTT GAACC GACGA TCTTC

GGG-3'

P5:
                                       (SEQ ID NO: 9)
5'-TGGTT GCGGG GGCCG GATTT-3'
```

First, P1 and P2 were annealed and elongated by Taq DNA polymerase. The resulting product was diluted 1:20 in PCR reaction buffer and amplified with P3 and P4 used as 5' and 3' primers, respectively. The product was further diluted 1:200 and amplified with P3 and P5 used as 5' and 3' primers, respectively, to give a DNA corresponding to tRNA$^{fMet}_{CAU}$. Then, the DNA product was transcribed with T7 RNA polymerase, and the transcript was purified by 10% denaturing PAGE. The resulting tRNA$^{fMet}_{CAU}$ was dissolved in water and the concentration was adjusted to 200 µM.

Similarly, tRNA$^{EnAsn}_{NNN}$ was synthesized by in vitro transcription from template DNAs amplified with the following primers.

```
P6:
                                       (SEQ ID NO: 10)
5'-GTAATACGACTCACTATAGGCTCTGTAGTTCAGTCGGTAGAACGGCG

GA-3'

P7:
                                       (SEQ ID NO: 11)
5'-GAACCAGTGACATACGGATTNNNAGTCCGCCGTTCTACCGACT-3'

P8:
                                       (SEQ ID NO: 12)
5'-TGGCGGCTCTGACTGGACTCGAACCAGTGACATACGGA-3'

P9:
                                       (SEQ ID NO: 13)
5'-TGGCGGCTCTGACTGGACTC-3'
```

First, P6 and P7 were annealed and elongated by Taq DNA polymerase. At this time, the NNN sequence of P7 was designed to correspond to a sequence of an anticodon of a tRNA to be prepared. The resulting product was diluted 1:20 in PCR reaction buffer and amplified with P3 and P8 used as 5' and 3' primers, respectively. The product was further diluted 1:200 and amplified with P3 and P9 used as 5' and 3' primers, respectively, to give a DNA corresponding to tRNA$^{EnAsn}_{NNN}$. Then, the DNA product was transcribed with T7 RNA polymerase, and the transcript was purified by 10% denaturing PAGE. The resulting tRNA$^{EnAsn}_{NNN}$ was dissolved in water and the concentration was adjusted to 200 µM. Similarly, tRNA$^{Asn}_{NNN}$ (5'-GUAAUACGACUCAC-UAUAGCCUCUGUAGUUCAGUCGGUA-GAACGGCGGAC UNNNAAUCCGUAUGUCACUGG-UUCGAGUCCAGUCAGAGGCACCA-3') (SEQ ID NO: 14) was synthesized by the same process.

Further, tRNA$^{Asn-El}_{GAU}$ was synthesized as follows.

First, P6 and P10 (P7 wherein the NNN sequence is ATC) were annealed and elongated by Taq DNA polymerase. The resulting product was diluted 1:20 in PCR reaction buffer and amplified with P3 and P8 used as 5' and 3' primers, respectively, to give a DNA corresponding to tRNA$^{Asn-El}_{GAU}$. Then, the DNA product was transcribed with T7 RNA polymerase in the presence of 10 mM GMP, and the transcript was purified by 8% denaturing PAGE. The resulting tRNA$^{Asn-El}_{GAU}$ was dissolved in water and the concentration was adjusted to 200 µM.

The ribozymes (I) and (II) were also synthesized by in vitro transcription. Specifically, ribozymes (I) and (II) were synthesized by the processes described in WO 2007/066627 and H. Murakami, A. Ohta, H. Ashigai, H. Suga (2006) "The flexizyme system: a highly flexible tRNA aminoacylation tool for the synthesis of nonnatural peptides" Nature Methods 3, 357-359.

3. Translation

In the present example, polypeptides having a desired nonnatural amino acid were translationally synthesized by adding a tRNA acylated with various amino acids to a cell-free translation system to initiate a translation.

The translation system used was PURESYSTEM® from PGI, which is a prokaryotic-derived reconstructed cell-free protein synthesis system including a transcription system from cDNA. Acylated tRNAs were added to translation reaction mixtures containing only minimum necessary amino acids.

First, an acylated tRNA for use in the translation reaction was prepared. In 0.1 M Hepes-K buffer pH 7.5, 0.1 M KCl, 600 mM MgCl₂, 15 µL of 20 µM ribozyme (I) or (II), 20 µM tRNA (tRNA$^{fMet}_{CAU}$, tRNA$^{EnAsn}_{NNN}$ and tRNA$^{Asn}_{NNN}$ having an anticodon of interest), and 5 mM substrate were reacted with 20% DMSO at 0° C. for 2 hours, and then the mixture was precipitated with ethanol to isolate a tRNA acylated with an amino acid of interest. Specifically, 40 µM tRNA was added to 0.2M Hepes-K buffer pH 7.5, 0.2 M KCl (7.5 µL), and the mixture was heated at 95° C. for 3 minutes and cooled to 25° C. in 5 minutes. MgCl₂ (3 M, 3 µL) and ribozyme (I) or (II) (200 µM, 1.5 µL) were added, and the mixture was allowed to stand at 25° C. for 5 minutes. An acylation reaction was started by adding a substrate (25 mM in DMSO, 3 µL), and the mixture was allowed to stand on ice for 2 hours. After the acylation reaction, the reaction was quenched by adding 45 μL of 0.6 M sodium acetate (pH 5), and RNA was recovered by ethanol precipitation. The pellet was washed twice with 70% ethanol and 0.1M sodium acetate (pH 5), and once with 70% ethanol to give an acylated tRNA. The acylated tRNA was dissolved in 0.5 μL of 1 mM sodium acetate immediately before it was added to a translation mixture.

Translational synthesis of peptides was performed by adding 0.04 μM cDNA, 200 μM minimum necessary amino acids (dependent on the cDNA sequence that was used) for elongation reaction, and 120 μM acylated tRNA to a translation reaction mixture using a PURE system, and allowing the mixture to stand at 37° C. for 1 hour.

Thereafter, the peptides were purified by one of the following two processes.

Peptides having a FLAG tag at C-termini of peptide sequences were purified with a FLAG tag antibody. ANTI-FLAG® M2 agarose commercially available from SIGMA was used as the FLAG antibody. First, the translation product was attached to the ANTI-FLAG® M2 agarose in 0.1 M Tris buffer pH 8.0, 0.15 M NaCl. The carrier was washed with a washing buffer (0.1 M Tris buffer pH 8.0, 0.15 M NaCl), and then 0.2% TFA solution was added to elute and isolate the translation product.

Peptides having no FLAG tag were purified by centrifugal ultrafiltration. Microcon YM-10 of Millipore (cutoff molecular mass: 10000) was used as a centrifugal filter unit. The translation product was diluted 1:6 with water, and the diluted translation product was moved to the Microcon and centrifuged at 14000×g for 30 minutes. The filtrate was recovered to purify the translation product.

MALDI-MS spectra of the purified translation product were measured using alpha-cyano-4-hydroxycinnamic acid as a matrix.

Example 1

Synthesis of Thioether Cyclized Peptides No. 1 (G7-18NATE)

G7-18NATE (compound of formula (16)) was translationally synthesized by the following two processes.

Example 1-1

Figure 4:
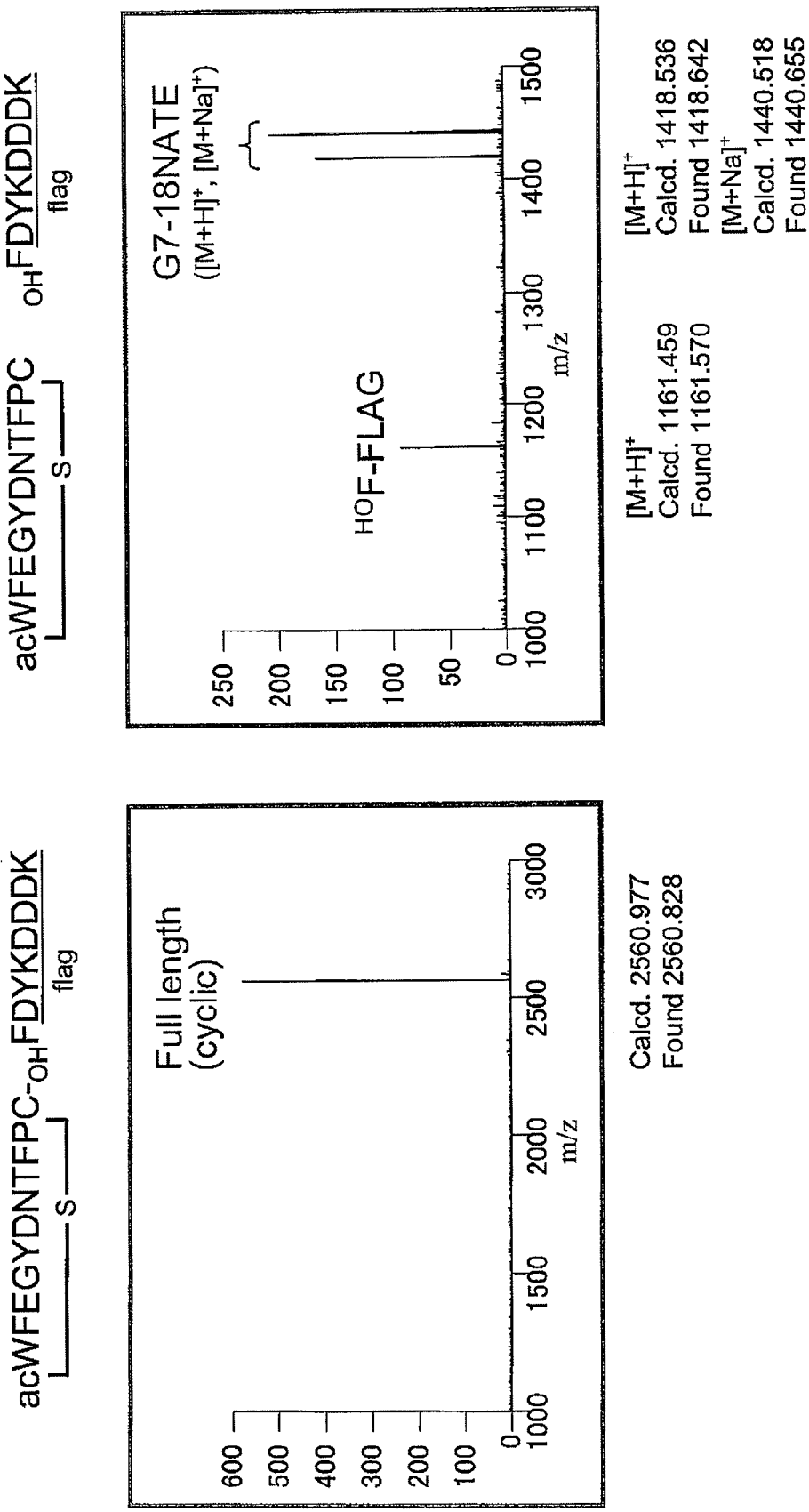
FIG. 4 (SEQ ID NOS: 28 and 40) shows mass spectra of the cyclic peptide compound of Example 1-1.

In the first process, the translational synthesis was performed using as a template DNA (5'-GCATATGTAATAC-GACTCACTATAGGGTTAACTTTAACAAG-GAGAAAAACATGT TTGAAGGTTATGACAATACCTTTCCGT-GCCTCGACTACAAGGACGACGACGACAA GTAAGCTTCG-3'/3'-CGTATACATTATGCTGAGT-GATATCCCAATTGAAATTGTTCCT CTTTTTGTA-CAAACTTCCAATACTGTTATGGAAAG-GCACGGAGCTGATGTTCCTGC TGCTGCTGTTCATTCGAAGC-5') (SEQ ID NO: 15). Exogenous acylated tRNAs that were added to the reaction system are $^{Cl}$acW-tRNA$^{fMet}_{CAU}$ (tRNA$^{fMet}_{CAU}$ aminoacylated with an amino acid compound of formula (19)) and $_{HO}$F-tRNA$^{EnAsn}_{GAG}$ (tRNA$^{EnAsn}_{GAG}$ acylated with phenyllactic acid). Amino acids that were added to the reaction system are Phe, Glu, Gly, Tyr, Asp, Asn, Thr, Pro, Cys, and Lys. Full-length cyclized peptides were confirmed by an MS spectrum (the left chart in FIG. 4). After purification by a FLAG antibody, a Bicine buffer (pH 9) was added, and the mixture was heated at 95° C. for 30 minutes to give peptide fragments of interest (MALDI-TOF, [M+H$^+$]: calculated 1418.536. found 1418.642, the right chart in FIG. 4).

Example 1-2

Figure 6:
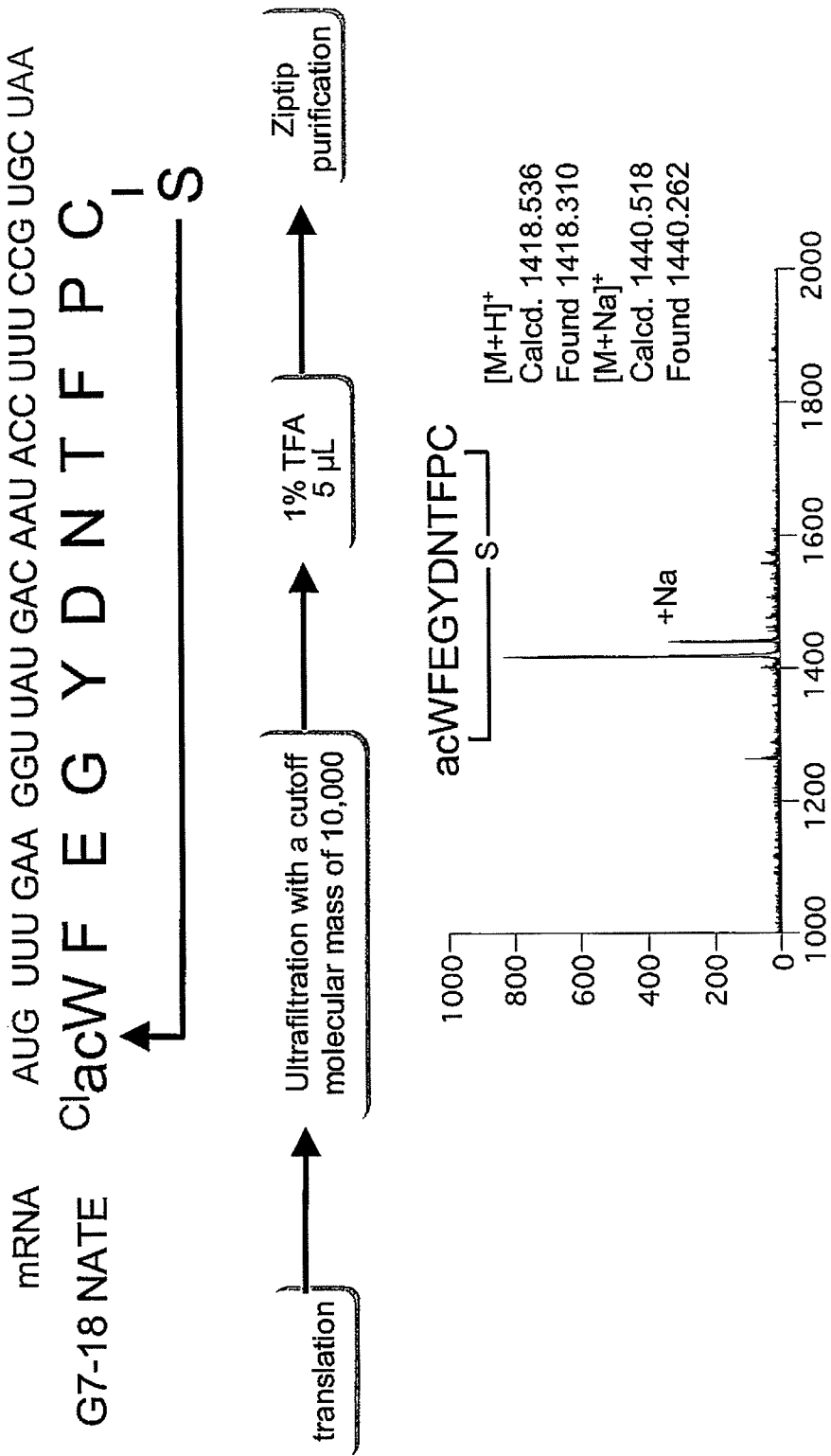
FIG. 6 (SEQ ID NOS: 41 and 28) shows a MALDI TOF of the cyclic peptide compound of Example 1-2.

In the second process, the translational synthesis was performed using as a template DNA (5'-GCATATGTAATAC-GACTCACTATAGGGTTAACTTTAACAAG-GAGAAAAACATGT TTGAAGGTTATGACAATACCTTTCCGT-GCTAAGCTTCG-3'/3'-CGTATACATTATGCT GAGT-GATATCCCAATTGAAATTGTTC-CTCTTTTTGTACAAACTTCCAATACTGTTAT GGAAAGGCACGATTCGAAGC-5') (SEQ ID NO: 16). Exogenous acylated tRNAs that were added to the reaction system are $^{Cl}$acW-tRNA$^{fMet}_{CAU}$ and $_{HO}$F-tRNA$^{EnAsn}_{GAG}$. Amino acids that were added to the reaction system are Phe, Glu, Gly, Tyr, Asp, Asn, Thr, Pro, and Cys. After the translation reaction was completed, purification was performed by ultrafiltration. It was confirmed from a MS spectrum that peptides of interest were synthesized (MALDI-TOF, [M+H$^+$]: calculated 1418.536. found 1418.310, FIG. 6).

Figure 5:
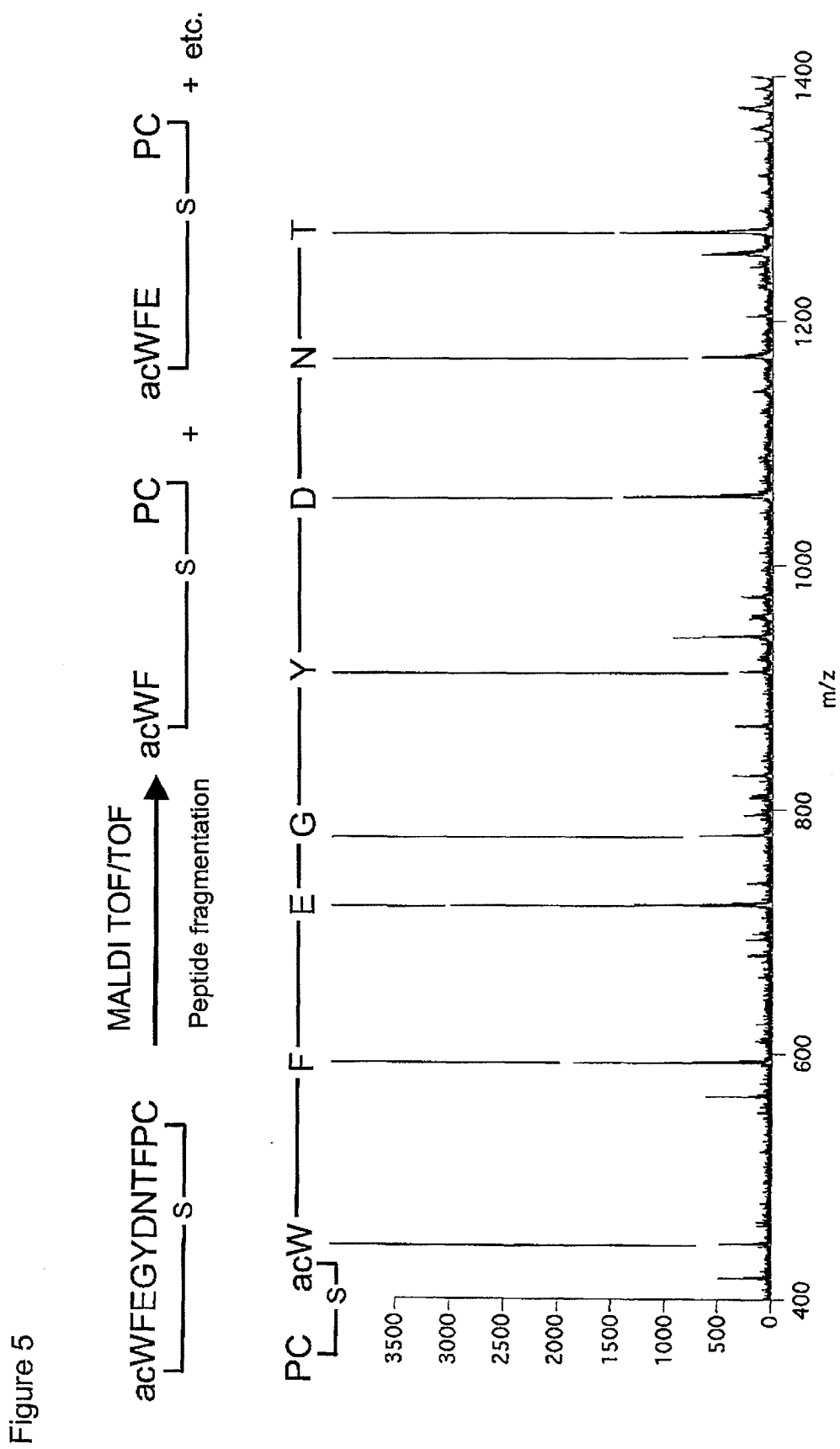
FIG. 5 (SEQ ID NO: 28) shows a MALDI TOF/TOF of a cyclic peptide compound of Example 1-2.

The post source decay of the resulting peptides was observed by MALDI-TOF/TOF tandem mass spectrometry, and it was confirmed that peptides were G7-18NATE of interest (refer to FIG. 5).

Example 2

Synthesis of Thioether Cyclized Peptide No. 2

Figure 8:
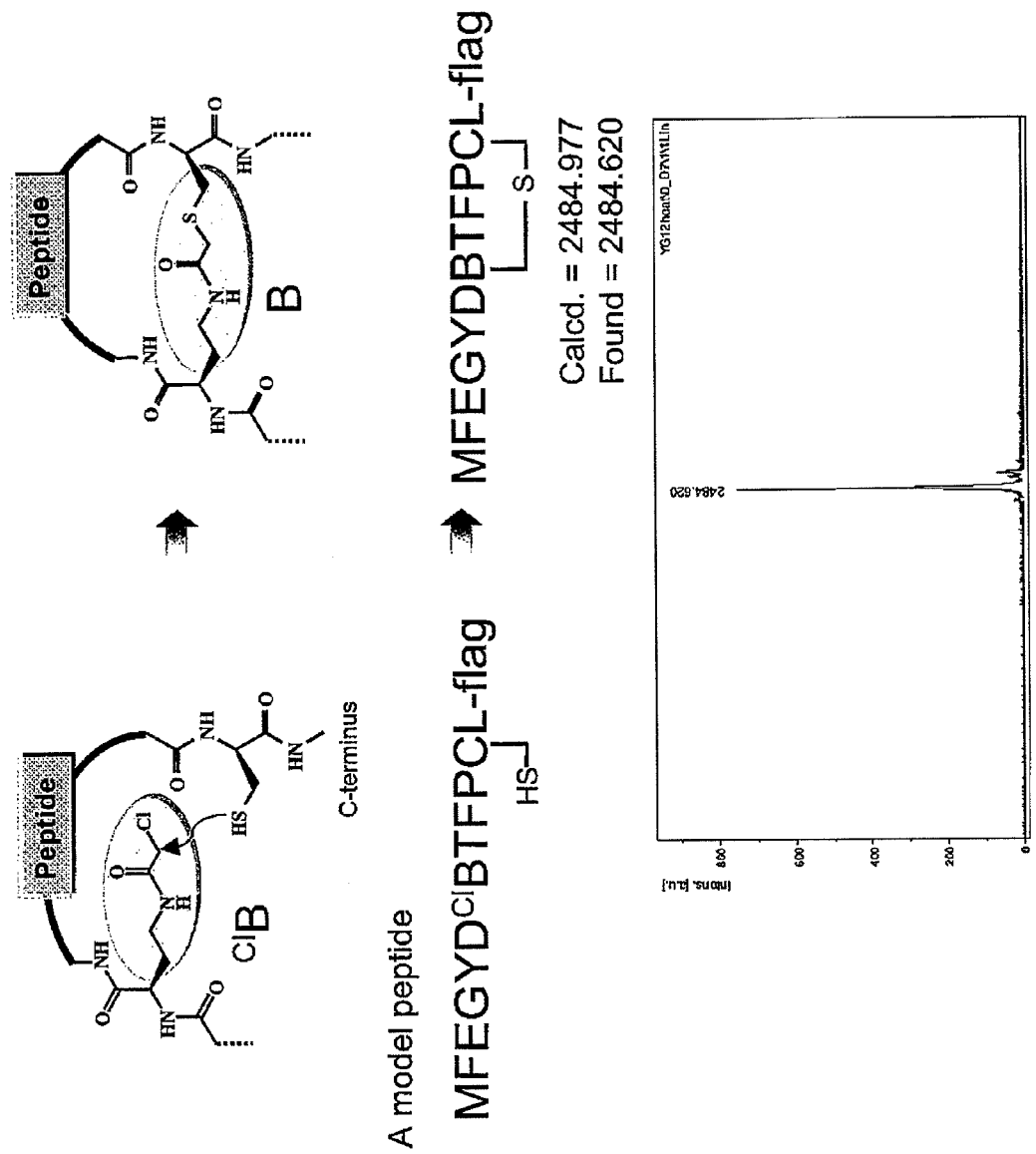
FIG. 8 (SEQ ID NO: 43) shows a cyclic peptide compound of Example 2 and a mass spectrum.

FIG. 8 illustrates development of cyclization after incorporation of $^{Cl}$B into model peptides. Peptides were translationally synthesized by the process described above in the item "3. Translation" using as a template DNA (5'-GCATAT-GTAATACGACTCACTATAGGGTTAACTT-TAACAAGGAGAAAAACATGT TTGAAGGTTATGA-CAATACCTTTCCGTGCCTCGACTACAAGGACGACG-ACGACAA GTAAGCTTCG-3'/3'-CGTATACATTATGCT-GAGTGATATCCCAATTGAAATTGTTCCT CTTTTTG-TACAAACTTCCAATACTGTTATGGAAAG-GCACGGAGCTGATGTTCCTGC TGCTGCTGTTCATTCGAAGC-5') (SEQ ID NO: 17). Amino acids that were added are Met, Phe, Glu, Gly, Tyr, Asp, Thr, Pro, Cys, Leu, and Lys. An aminoacyl-tRNA that was added is $^{Cl}$B-tRNA$^{Asn}_{GUU}$ (tRNA$^{Asn}_{GUU}$ aminoacylated with an amino acid compound of formula (33)).

Purification by a FLAG antibody was performed by the process described above in the item "3. Translation." Analysis by MALDI-MS was performed, and it was confirmed that cyclization of the peptides was quantitatively developed (MALDI-MS, [M+H$^+$]: calculated 2484.977. found 2484.620, FIG. 8).

Example 3

Synthesis of Thioether Cyclized Peptide No. 3
(Urotensin II Analog YS9: Formula (35) (SEQ ID NO: 31))

[Formula 21]

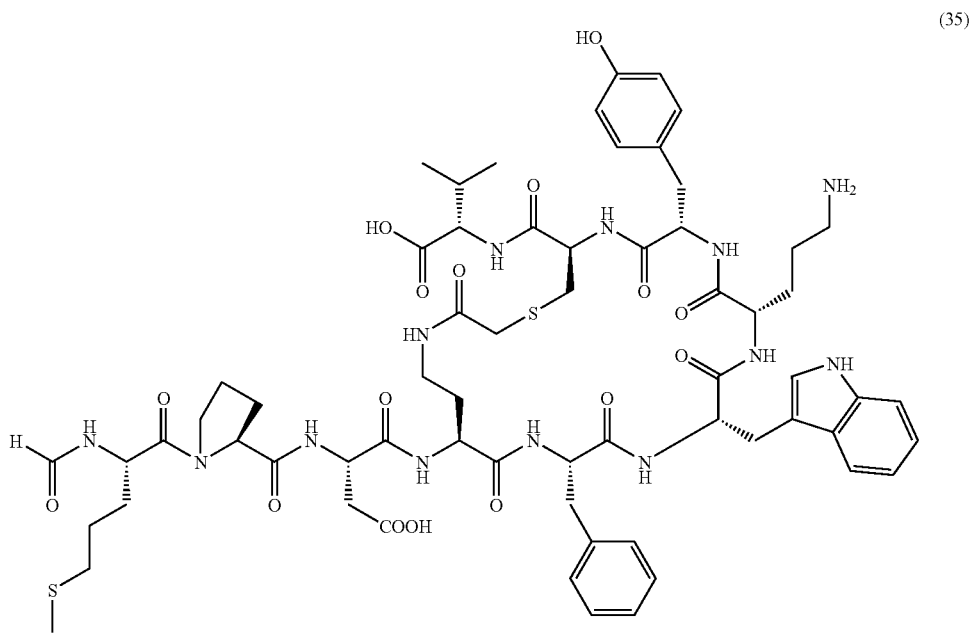

(35)

Figure 9:
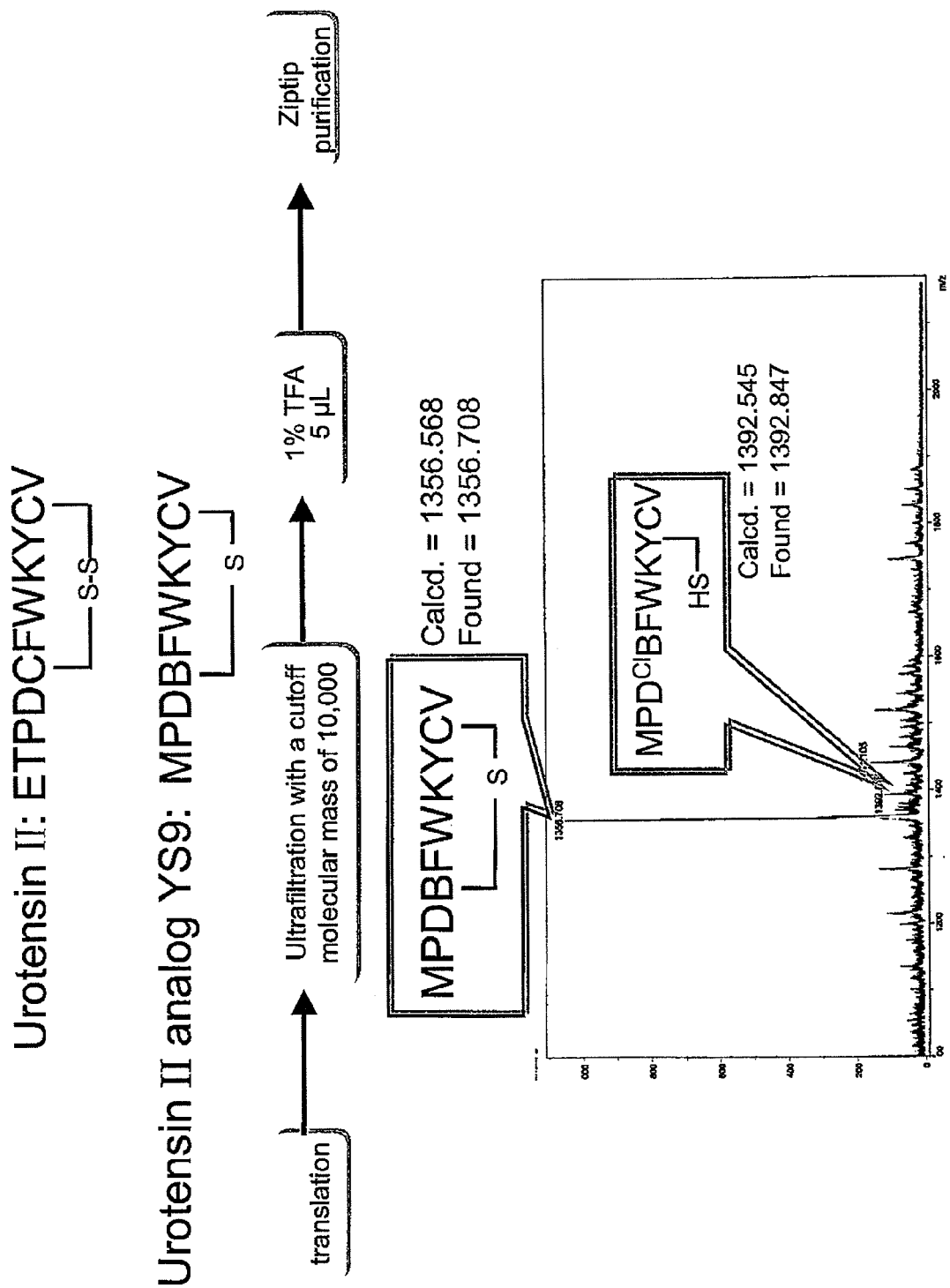
FIG. 9 (SEQ ID NO: 42 and 31) shows a cyclic peptide compound (Urotensin II analog) of Example 3 and a mass spectrum.

In FIG. 9, YS9 was translationally synthesized by the process described above in the item "3. Translation" using as a template DNA (5'-TAATACGACTCACTATAGGGT-TAACTTTAACAAGGAGAAAAACATGCCG-GACCTCTT CTGGAAGTACTGTGTTTAAGCTTCG-3'/3'-ATTATGCTGAGTGATATCCCAATTGAAATTGTTCC-TCTTTTTGTACGGCCTGGAGAAG ACCTTCATGACA-CAAATTCGAAGC-5') (SEQ ID NOS: 18 and 51). Amino acids that were added are Met, Pro, Asp, Phe, Trp, Lys, Tyr, Cys, and Val. An aminoacyl-tRNA that was added is $^{ClAsn}$B-tRNA$^{Asn}_{GUU}$.

The peptides were purified by ultrafiltration by the process described above in the item "3. Translation" and analyzed by MALDI-MS. It was confirmed that most of the peptides were cyclized (MALDI-MS, [M+H$^+$]: calculated 1356.568. found 1356.708, FIG. 9).

Calcium Mobilization Measurement

Figure 10:
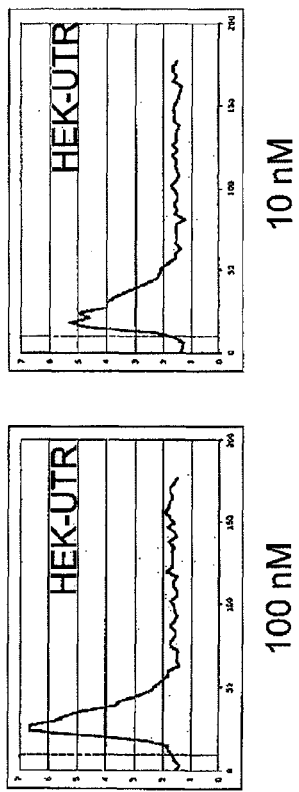
FIG. 10 (SEQ ID NOS: 42, 44 and 31) illustrates calcium mobilization experiments on Urotensin II and the cyclic peptide compound (Urotensin II analog) of Example 3.
Figure 10:
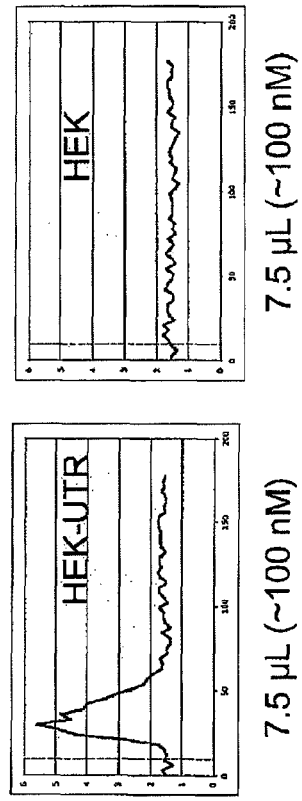
Figure 10:
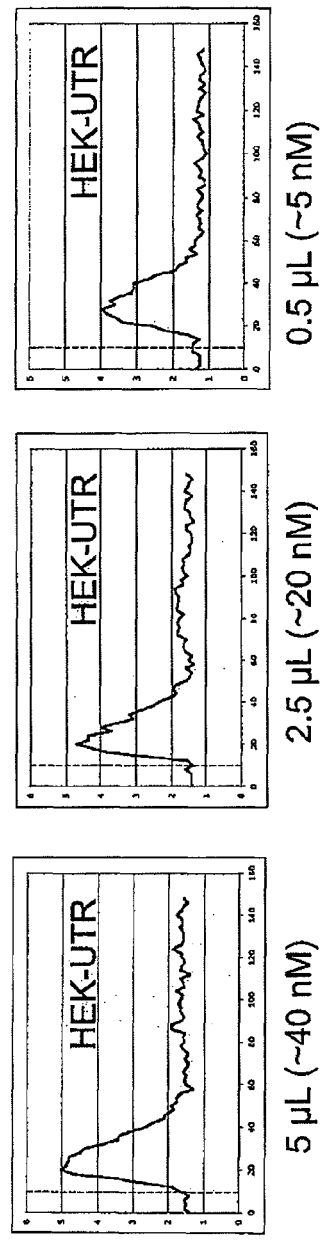

FIG. 10 illustrates calcium mobilization in cells by addition of peptides using a fluorescent reagent. $2 \times 10^5$ HEK-UTR cells (HEK cells expressing an Urotensin II receptor) were seeded into a 96 well plate. After 12-16 hours, the cells were incubated in 1 µM Fluo-4-AM (Dojindo Laboratories) for 1 hour. After the incubation was completed, the fluorescent reagent was removed, and 90 µL of an assay buffer (Hanks Balanced Salts Solution (HBSS), 10 mM HEPES, 200 µM of CaCl$_2$, 0.1% BSA, and 2.5 mM probenecid) was added. Then, 10 µL of peptides dissolved in an assay buffer was added, and changes in an intensity of fluorescent light were measured by a microplate reader. The peptides were prepared by purifying the translation product by Zip-tip (Millipore) and distilling off the elute under reduced pressure.

YS4 peptides (FIG. 10) were translationally synthesized by the process described above in the item "3. Translation" using as a template DNA (5'-TAATACGACTCACTAT-AGGGTTAACTTTAACAAGGAGAAAAA-CATGCCGGACTGTTT CTGGAAGTACTGTGTT-TAAGCTTCG-3'/3'-ATTATGCTGAGTGATATCCCAATTGAAA-TTGTTCCTCTTTTTGTACGGCCTGACAAAG ACCT-TCATGACACAAATTCGAAGC-5') (SEQ ID NOS: 19 and 52) Amino acids that were added are Met, Pro, Asp, Phe, Trp, Lys, Tyr, Cys, and Val.

When Urotensin II (Peptide Institute, Inc.) was added as a control to the HEK-UTR cells, a change in the concentration of calcium was observed. The same response was obtained when YS4 peptides having a disulfide bond were added. On the other hand, no response was obtained when YS4 peptides were added to HEK cells that did not express an Urotensin II receptor. When thioether cyclized peptides YS9 were added to the HEK-UTR cells, calcium mobilization in the cells was observed as in the case of Urotensin II.

Protease Resistance of Thioether Cyclized Peptides

Figure 11:
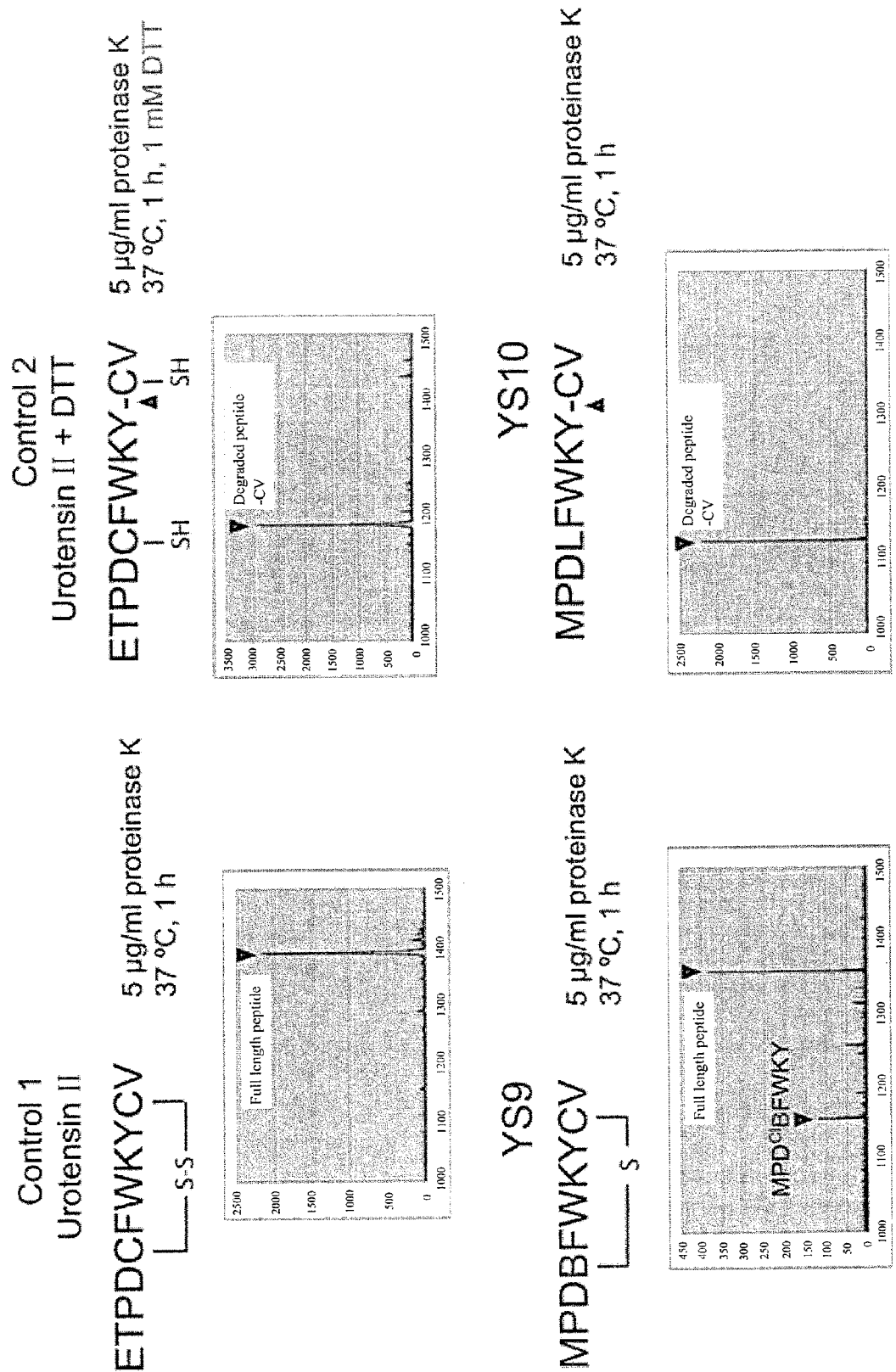
FIG. 11 (SEQ ID NOS: 42, 31 and 45) illustrates protease resistance experiments on Urotensin II and the cyclic peptide compound of Example 3.

FIG. 11 shows protease resistance of the peptides. Translationally synthesized peptides and purchased Urotensin II peptides were reacted in 5 µg/ml of a proteinase K solution at 37° C. for 1 hour in the presence of, or in the absence of, 1 mM DTT.

Linear peptides YS10 were translationally synthesized using the same template DNA as that used in the synthesis of the YS9 peptides. Amino acids that were added are Met, Pro, Asp, Leu, Phe, Trp, Lys, Tyr, Cys, and Val.

It was found from analysis by MALDI-MS that while the Urotensin II peptides were not degraded by proteinase K, the peptides that were changed into a linear form were decomposed by the DTT. It was also found that while the cyclic YS9 peptides were not degraded by proteinase K, the linear peptides YS10 were degraded.

Example 4

Figure 12:
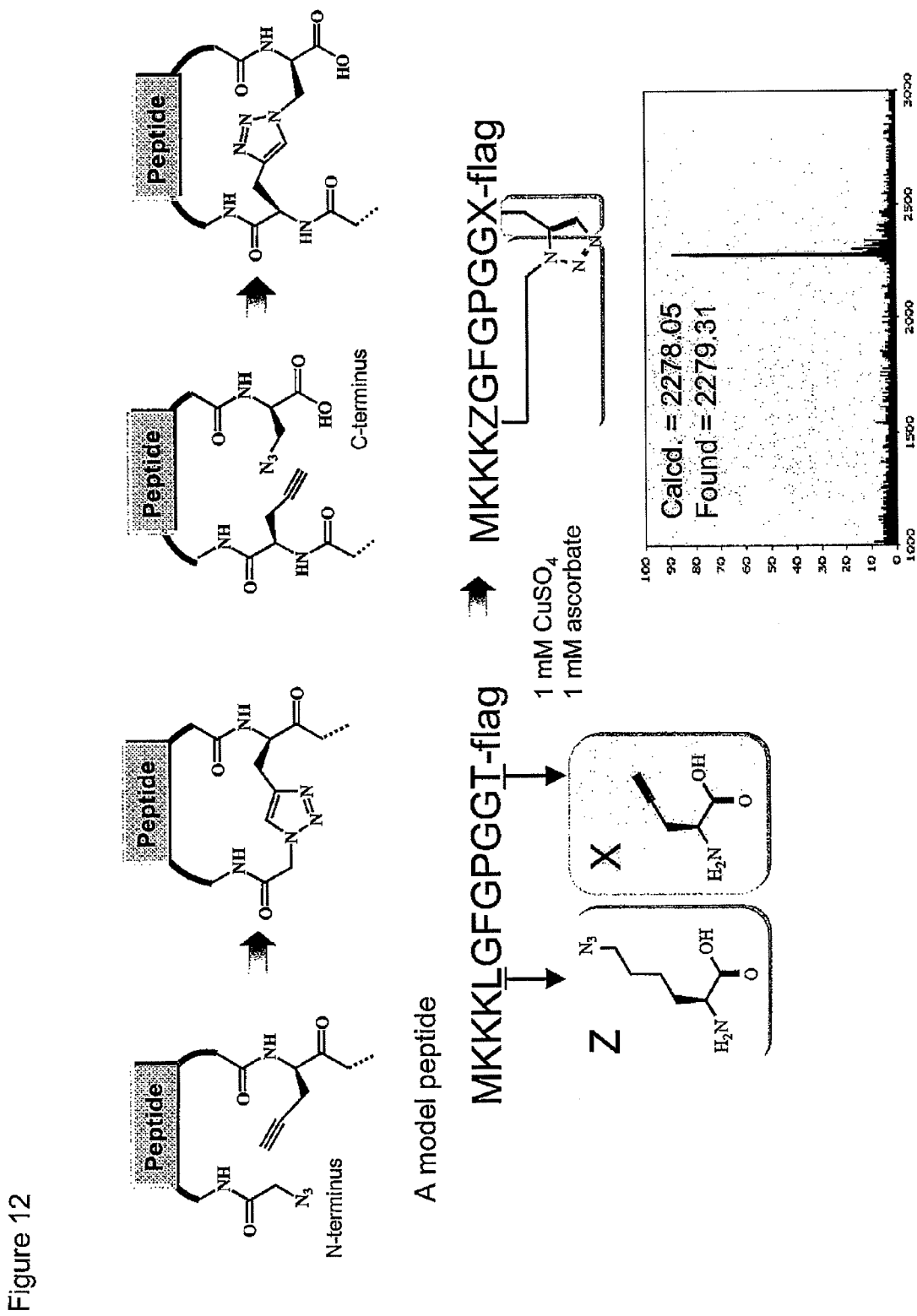
FIG. 12 (SEQ ID NOS: 46 and 32) shows a cyclic peptide compound of Example 4 and a mass spectrum.

Synthesis of Triazole Cyclic Peptide Compound (FIG. 12)

As shown in FIG. 12, an amino acid having an azido group and an acetylene group was incorporated into model peptides. The model peptides were translationally synthesized by the process described above in the item "3. Translation" using as a template DNA (5'-TAATACGACTCACTATAGGGCTT-TAATAAGGAGAAAAACATGACCCCGGACTGTTTC TGGAAGTACTGTGTTCTCGAAGAAGAC-TACAAGGACGACGACGACAAGTAAGCTTC G-3'/3'-ATTATGCTGAGTGATATCCCGAAATTAT-TCCTCTTTTTGTACTGGGGCCTGACAAAG ACCTTCATGACACAAGAGCTTCTTCT-GATGTTCCTGCTGCTGCTGTTCATTCGAAGC-5') (SEQ ID NOS: 20 and 53). Amino acids that were added are Met, Lys, Gly, Phe, Pro, Asp, and Tyr Aminoacyl-tRNAs that were added are Z-tRNA$^{Asn}_{GAG}$ (tRNA$^{Asn}_{GAG}$ aminoacylated with an amino acid compound of formula (5) wherein m is 4) and X-tRNA$^{Asn}_{GGU}$ (tRNA$^{Asn}_{GGU}$ aminoacylated with the amino acid compound of formula (6) wherein m is 1).

After the translational synthesis was completed, the peptides were purified by a FLAG antibody and reacted in 1 mM CuSO$_4$ and 1 mM ascorbic acid at room temperature for 1 hour to develop cyclization reaction. The peptides were reacted overnight in 50 mM TCEP (tris(2-carboxyethyl) phosphine) and then analyzed by MALDI-MS to determine cyclization efficiency; no reduced peptide was observed. It was confirmed from the result that the azido group in the peptides quantitatively reacted with the acetylene group to form a cyclicpeptide (formula (36) (SEQ ID NO: 32)).

[Formula 22]

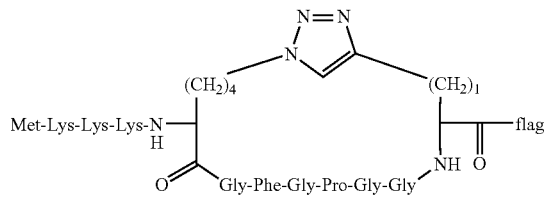

(36)

Example 5

Synthesis of Cyclized Peptides having Fluorescent Light

Five processes for the synthesis of cyclized peptides having fluorescent light are described below.

Example 5-1

Figure 13:
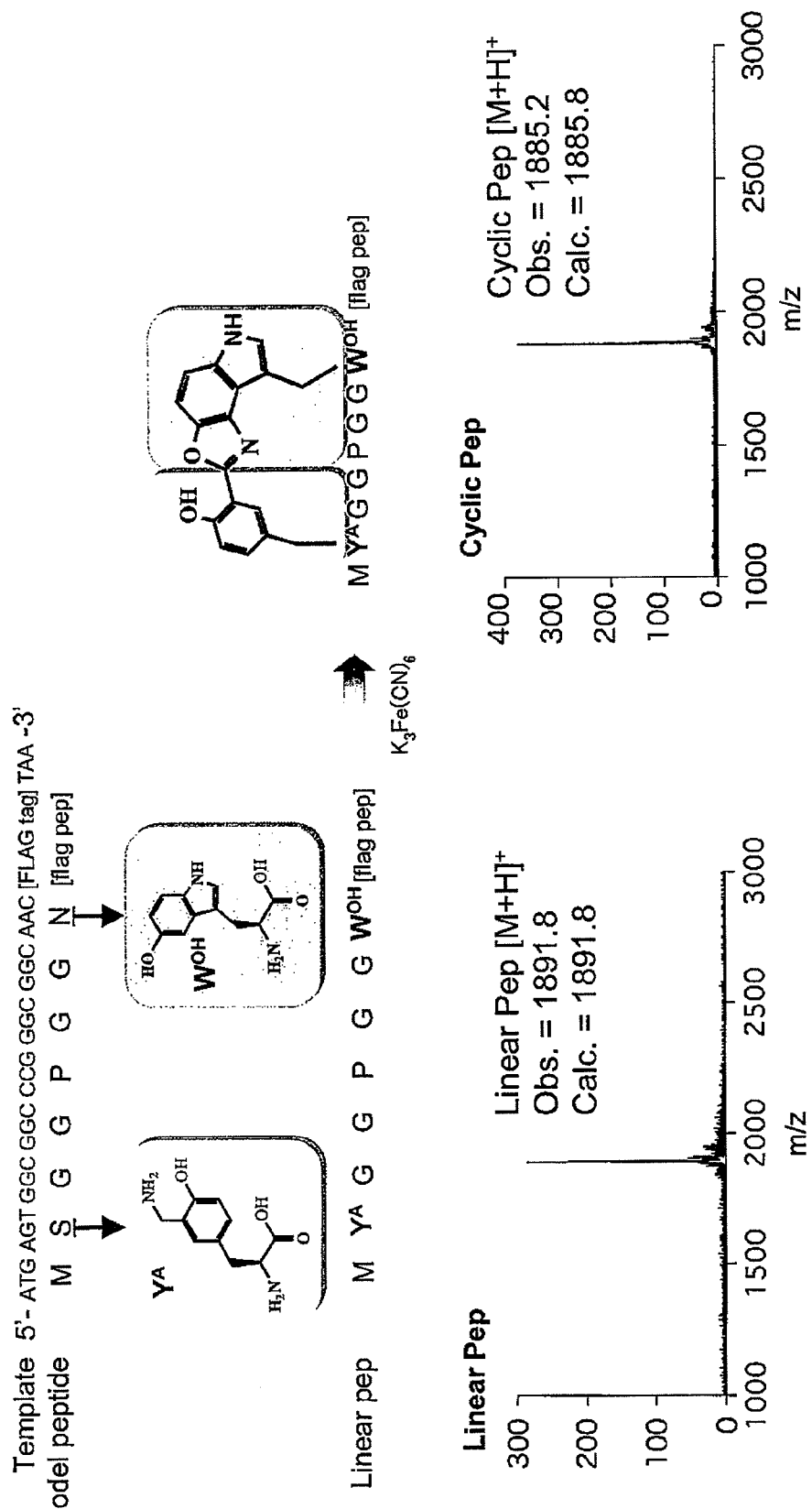
FIG. 13 (SEQ ID NOS: 47, 48 and 49) shows a cyclic peptide compound of Example 5-1 and mass spectra.

Peptide having Y$^A$ at the serine moiety of the model peptide and W$^{OH}$ at the asparagine moiety of the model peptide was synthesized (FIG. 13). K$_3$Fe(CN)$_6$ (final concentration 30 mM) was added to the peptide in a Borate buffer (final concentration 250 mM, pH 9.0), and the mixture was reacted at room temperature for 10 minutes. The product was analyzed by MALDI-MS, and it was confirmed that cyclization reaction was developed almost quantitatively (MALDI-MS, [M+H$^+$]: calculated 1885.8. found 1885.2, FIG. 13).

The model peptide was translationally synthesized by the process described above in the item "3. Translation" using as a template DNA (5'-TAATACGACTCACTATAGGGT-GATCCAACTTTAATAAGGAGGTATACCAATGAGTGG CGGCCCGGGCGGCAACGATTATAAAGAT-GATGATGATAAATAAGCTTCG-3'/3'-ATTATGCTGAGT-GATATCCCACTAGGTTGAAATTATTC-CTCCATATGGTTACTCACCG CCGGGCCCGCCGTTGCTAATATTTCTAC-TACTACTATTTATTCGAAGC) (SEQ ID NOS: 21 and 54). Amino acids that were added are Met, Gly, Pro, Asp, Tyr, and Lys. tRNAs that were added are Y$^A$-tRNA$^{Asn}_{ACU}$ (tRNA$^{Asn}_{ACU}$ aminoacylated with the amino acid compound of formula (32)) and W$^{OH}$-tRNA$^{Asn}_{GUU}$ (tRNA$^{Asn}_{GUU}$ aminoacylated with the amino acid compound of formula (8)). The cyclic peptide compound obtained in the present embodiment is the compound of formula (11).

Example 5-2

Figure 15:
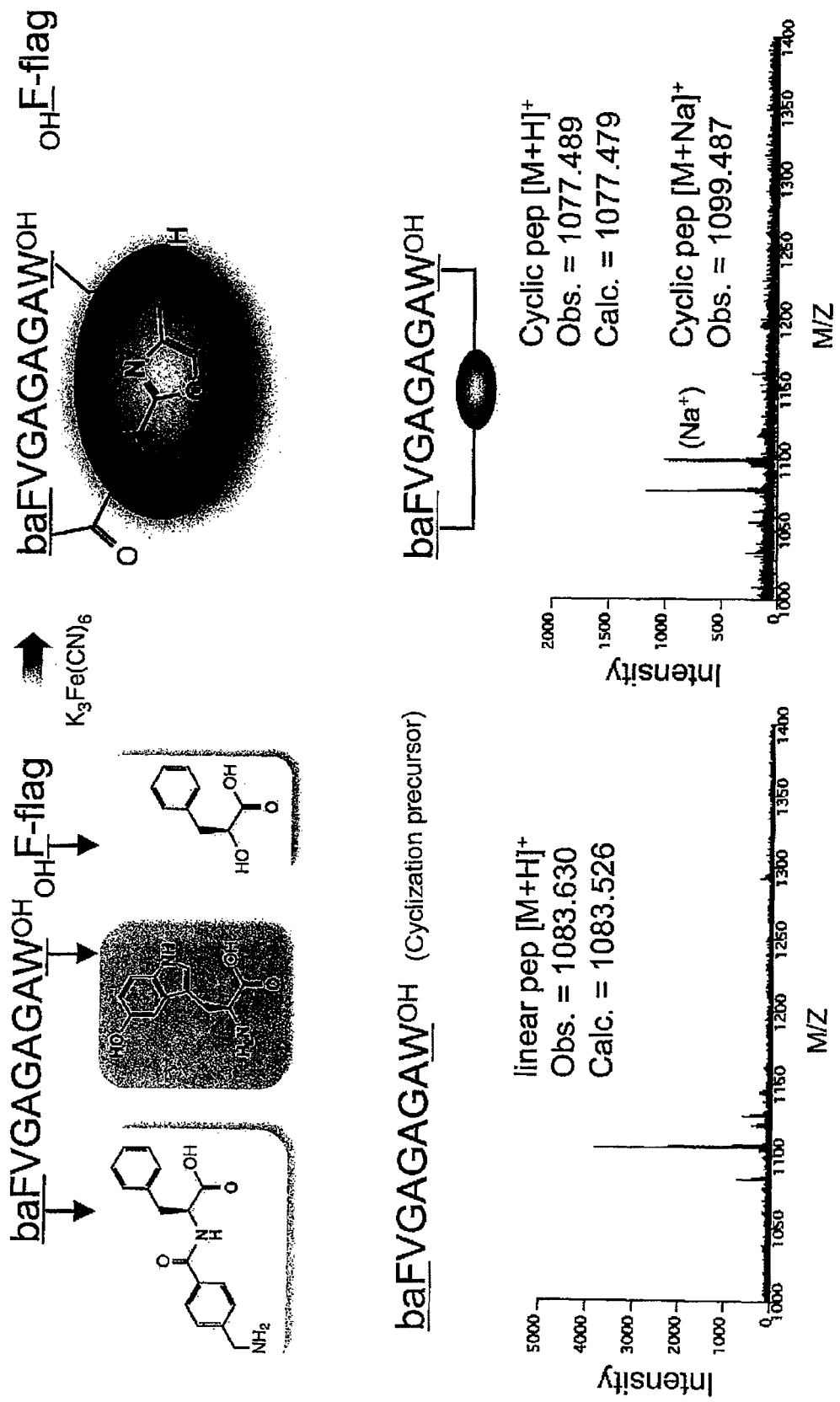
FIG. 15 (SEQ ID NO: 50) shows mass spectra of a cyclic peptide compound of Example 5-2.

Peptide having $^{ba}$F at the methionine moiety, W$^{HO}$ at the leucine moiety, and $_{HO}$F at the asparagine moiety was synthesized (FIG. 15). After the peptides were purified by a FLAG antibody, a Bicine buffer (final concentration 200 mM, pH 9) was added, and the mixture was heated at 95° C. for 30 minutes to give non-cyclic peptides (FIG. 15). K$_3$Fe(CN)$_6$ (final concentration 30 mM) was added to the non-cyclic peptides in a Borate buffer (final concentration 250 mM, pH 9.0), and the mixture was reacted at room temperature for 10 minutes. The product was analyzed by MALDI-MS, and it was confirmed that cyclized peptides were synthesized (FIG. 15). The peptides were translationally synthesized by the process described above in the item "3. Translation" using as a template DNA (5'-CGTATACTAATACGACTCACTAT-AGGGTTAACTTTAACAAGGAGAAAAACATGGTTG GTGCAGGTGCAGTTGGTGCACTCAAC-GACTACAAGGACGACGACGACAAGTAAGCT TCG-3'/3'-GCATATGATTATGCTGAGTGATATC-CCAATTGAAATTGTTCCTCTTTTTGTACCAACC ACGTCCACGTCAACCACGTGAGTTGCT-GATGTTCCTGCTGCTGCTGTTCATTCGAAG C-5') (SEQ ID NOS: 22 and 55). Amino acids that were added are Val, Gly, Ala, Asp, Tyr, and Lys. tRNAs that were added are $^{ba}$F-tRNA$^{fMet}_{CAU}$ (tRNA$^{fMet}_{CAU}$ aminoacylated with an amino acid compound of formula (31)), W$^{OH}$-tRNA$^{EnAsn}_{GAG}$, and $_{HO}$F-tRNA$^{EnAsn}_{GUU}$. The cyclic peptide compound obtained in the present example is the compound of formula (12).

Example 5-3

A peptide compound of formula (37) was translationally synthesized by the process described above in the item "3. Translation" using as a template DNA (5'-CGTATAC-TAATACGACTCACTATAGGGTTAACTT-TAACAAGGAGAAAAACATGCGA ACCCGAAGTC-CAGTTAACCTCGGTATCGACTAAGCTTCG-3'/3'-GCATATGATTATGCTGAGTGATATCCCAATTGAAAT-TGTTCCTCTTTTTGTACGCTTG GGCTTCAGGTCAAT-TGGAGCCATAGCTGATTCGAAGC-5') (SEQ ID NOS: 23 and 56), and amino acids Arg, Thr, Ser, Pro, Val, Asn, Leu, Gly, and Asp and W$^{OH}$-tRNA$^{Asn-El}_{GAU}$ and $^{bza}$F-tRNA$^{fMet}_{CAU}$ (tRNA$^{fMet}_{CAU}$ aminoacylated with $^{bza}$F-CME).

Then, cyclization reaction of the peptide compound was performed. To 5 μL of a translational synthesis reaction mixture, 2.5 μL of Borate buffer (1M, pH 8) and 2.5 μL of K₃Fe(CN)₆ aqueous solution (2.5 mM) were added, and the mixture was allowed to stand at room temperature for 5 minutes. The product was analyzed by MALDI-MS, and it was confirmed that cyclized peptides (formula (38), (SEQ ID NO: 33)) were synthesized (molecular mass of formula (37): calculated 1624.82. found 1624.65; molecular mass of formula (38): calculated 1618.78. found 1618.83).

[Formula 23]

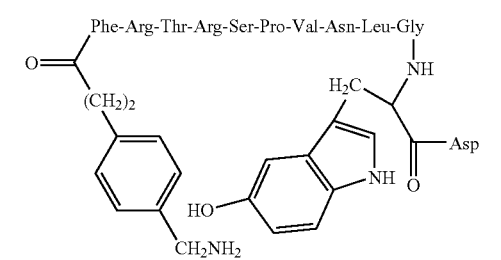

(37)

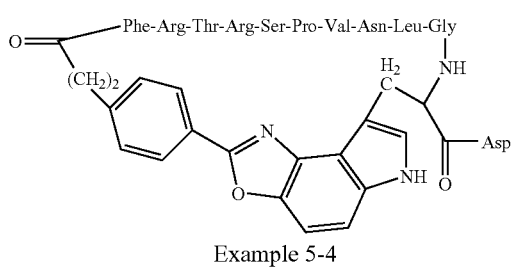

(38)

Example 5-4

A peptide compound of formula (39) was translationally synthesized by the process described above in the item "3. Translation" using as a template DNA (5'-CGTATAC-TAATACGACTCACTATAGGGTTAACTT-TAACAAGGAGAAAAACATGCGA ACCCGAAGTC-CAGTTAACATCGACTAAGCTTCG-3'/3'-GCATATGATTATGCTGAGTGATATCCCAATTGAAATT-GTTCCTCTTTTTGTACGCTTG GGCTTCAGGTCAAT-TGTAGCTGATTCGAAGC-5') (SEQ ID NOS: 24 and 57) Amino acids that were added are Arg, Thr, Ser, Pro, Val, Asn, and Asp. tRNAs that were added are $W^{OH}$-tRNA$^{Asn-El}_{GAU}$ and $^{bza}$F-tRNA$^{fMet}_{CAU}$.

Then, cyclization reaction of the peptide compound was performed as in Example 5-3. The product was analyzed by MALDI-MS, and it was confirmed that cyclized peptides (formula (40), (SEQ ID NO: 34)) were synthesized (molecular mass of formula (39): calculated 1454.72. found 1454.60; molecular mass of formula (40): calculated 1448.67. found 1448.51).

[Formula 24]

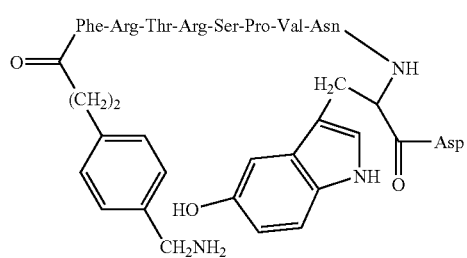

(39)

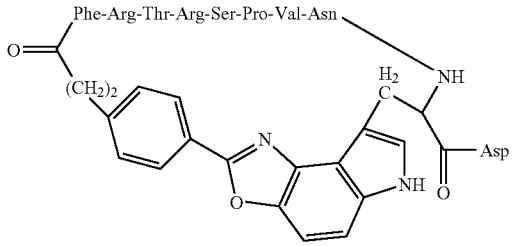

(40)

Example 5-5

A peptide compound of formula (41) was translationally synthesized by the process described above in the item "3. Translation" using as a template DNA (5'-CGTATAC-TAATACGACTCACTATAGGGTTAACTT-TAACAAGGAGAAAAACATGCGA ACCCGAAGTC-CAATCGACTAAGCTTCG-3'/3'-GCATATGATTATG-CTGAGTGATATCCCAATTGAAATTGTTC-CTCTTTTTGTACGCTTG GGCTTCAGGTTAGCTGAT-TCGAAGC-5') (SEQ ID NOS: 25 and 58) Amino acids that were added are Arg, Thr, Ser, Pro, and Asp. tRNAs that were added are $W^{OH}$-tRNA$^{Asn-El}_{GAU}$ and $^{bza}$F-tRNA$^{fMet}_{CAU}$.

Then, cyclization reaction of the peptide compound was performed as in Example 5-3. The product was analyzed by MALDI-MS, and it was confirmed that cyclized peptides (formula (42), (SEQ ID NO: 35)) were synthesized (molecular mass of formula (41): calculated 1241.61. found 1241.39; molecular mass of formula (42): calculated 1235.56. found 1235.38).

[Formula 25]

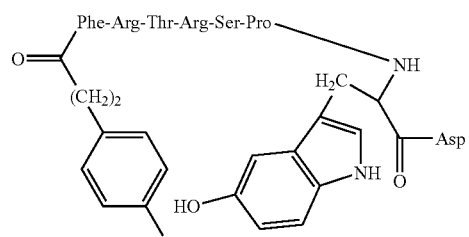

(41)

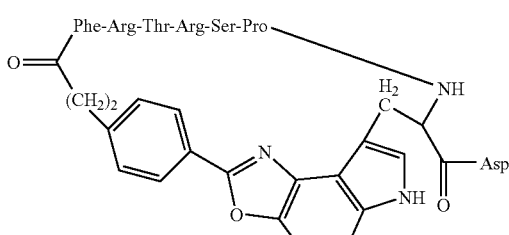

(42)

Example 5-6

A peptide compound of formula (43) was translationally synthesized by the process described above in the item "3. Translation" using as a template DNA (5'-CGTATAC-TAATACGACTCACTATAGGGTTAACTT-TAACAAGGAGAAAAACATGCGA ACCCGAATCGAC-TAAGCTTCG-3'/3'-

GCATATGATTATGCTGAGTGATATCCCAATTGAAATT-GTTCCTCTTTTTGTACGCTTG GGCTTAGCTGATTC-GAAGC-5') (SEQ ID NOS: 26 and 59) Amino acids that were added are Arg, Thr, and Asp. tRNAs that were added are $W^{OH}$-tRNA$^{Asn-El}{}_{GAU}$ and $^{bza}$F-tRNA$^{fMet}{}_{CAU}$.

Then, cyclization reaction of the peptide compound was performed as in Example 5-3. The product was analyzed by MALDI-MS, and it was confirmed that cyclized peptides (formula (44) (SEQ ID NO: 36)) were synthesized (molecular mass of formula (43): calculated 1057.52. found 1057.23; molecular mass of formula (44): calculated 1051.47. found 1051.23).

[Formula 26]

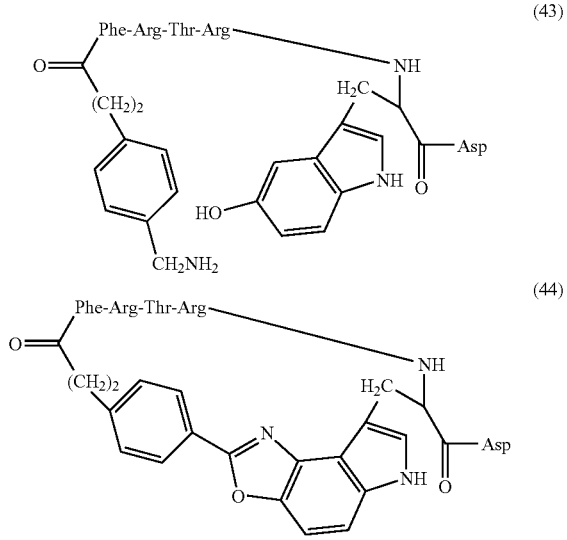

Figure 14:
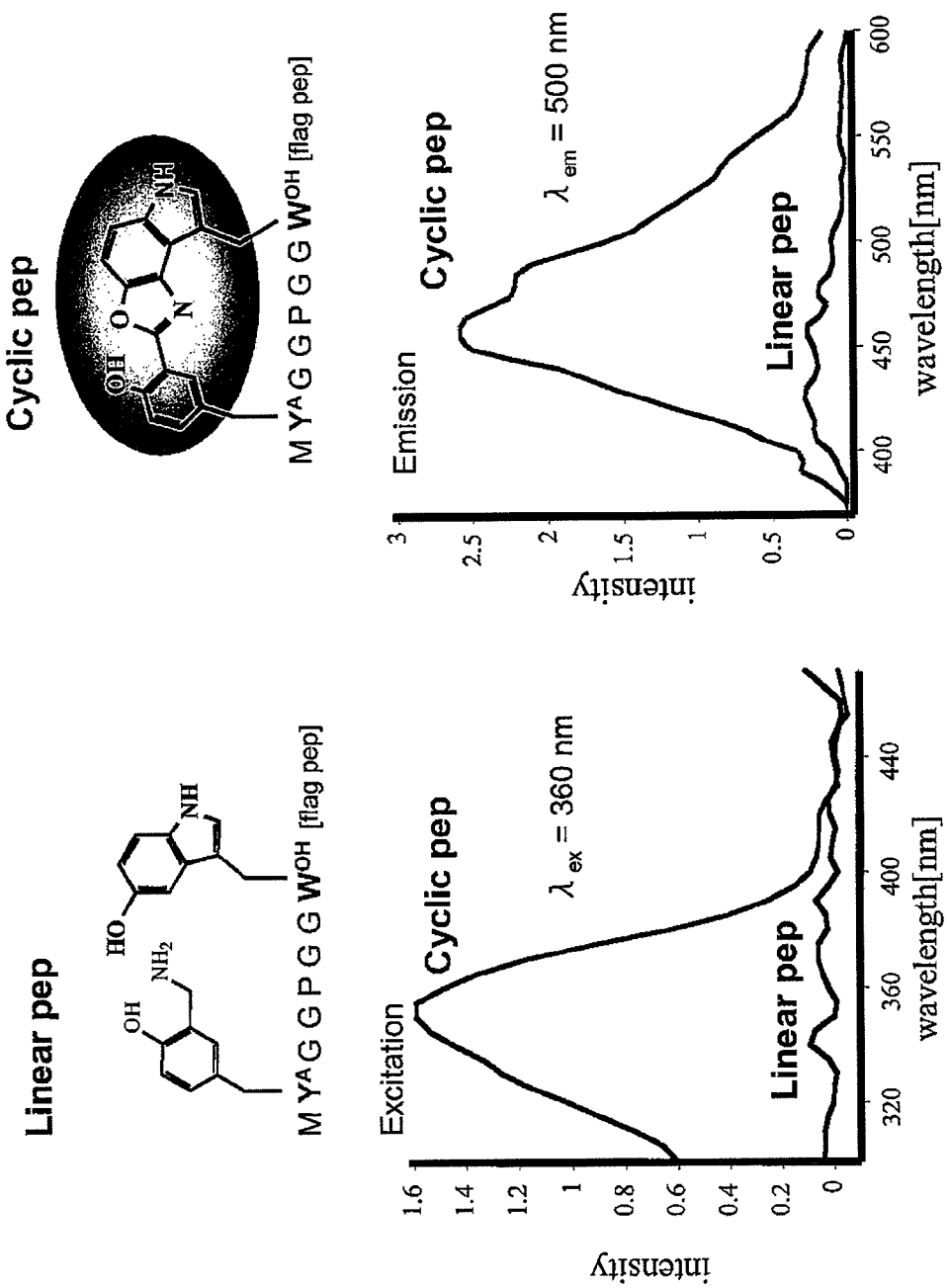
FIG. 14 (SEQ ID NO: 49) shows fluorescence spectra of the cyclic peptide compound of Example 5-1.

Measurement of Fluorescent Light of Fluorescent Cyclized Peptides (FIG. 14)

Excitation and fluorescence spectra of non-cyclic and cyclic peptides were measured. Each peptide was dissolved in a 250 mM Borate buffer (pH 9.0) and 25% acetonitrile solution. Excitation spectra were measured at a fluorescence wavelength of 500 nm, and fluorescence spectra were measured at an excitation wavelength of 360 nm. While no specific spectrum was observed in the case of the non-cyclic peptides, emission of fluorescent light was observed in the case of the cyclized peptides.

[Sequence List Free Text]
SEQ ID NO: 1: initiator tRNA (tRNA$^{fMet}$)
SEQ ID NO: 2: initiator tRNA with a modified anticodon
SEQ ID NO: 3: ribozyme I
SEQ ID NO: 4: ribozyme II
SEQ ID NO: 5: P1
SEQ ID NO: 6: P2
SEQ ID NO: 7: P3
SEQ ID NO: 8: P4
SEQ ID NO: 9: P5
SEQ ID NO: 10: P6
SEQ ID NO: 11: P7
SEQ ID NO: 12: P8
SEQ ID NO: 13: P9
SEQ ID NO: 14: tRNA (tRNA$^{Asn}{}_{NNN}$)
SEQ ID NO: 15: template DNA1
SEQ ID NO: 16: template DNA2
SEQ ID NO: 17: template DNA3
SEQ ID NO: 18: template DNA4
SEQ ID NO: 19: template DNA5
SEQ ID NO: 20: template DNA6
SEQ ID NO: 21: template DNA7
SEQ ID NO: 22: template DNA8
SEQ ID NO: 23: template DNA9
SEQ ID NO: 24: template DNA10
SEQ ID NO: 25: template DNA11
SEQ ID NO: 26: template DNA12
SEQ ID NO: 27: a peptide to be attached to a SH2 domain of Grb7
SEQ ID NO: 28: a peptide moiety of the compound of formula (16)
SEQ ID NO: 29: a peptide moiety of the compound of formula (11)
  Xaa is derived from a tyrosine derivative
  Xaa is derived from a tryptophan derivative
SEQ ID NO: 30: a peptide moiety of the compound of formula (12)
  Xaa is derived from a phenylalanine derivative
  Xaa is derived from a tryptophan derivative
SEQ ID NO: 31: a peptide moiety of the compound of formula (35)
  Xaa is derived from a derivative of 2,4-diaminobutyric acid
SEQ ID NO: 32: a peptide moiety of the compound of formula (36)
  Xaa is derived from 2-amino-6-azidohexanoic acid
  Xaa is derived from 2-amino-4-pentynoic acid
SEQ ID NO: 33: a peptide moiety of the compound of formula (38)
  Xaa is derived from a phenylalanine derivative
  Xaa is derived from a tryptophan derivative
SEQ ID NO: 34: a peptide moiety of the compound of formula (40)
  Xaa is derived from a phenylalanine derivative
  Xaa is derived from a tryptophan derivative
SEQ ID NO: 35: a peptide moiety of the compound of formula (42)
  Xaa is derived from a phenylalanine derivative
  Xaa is derived from a tryptophan derivative
SEQ ID NO: 36: a peptide moiety of the compound of formula (44)
  Xaa is derived from a phenylalanine derivative
  Xaa is derived from a tryptophan derivative

The invention claimed is:

1. A process for synthesizing a cyclic peptide compound, comprising the steps of:
   (1) translationally synthesizing a non-cyclic peptide compound comprising non-natural amino acid(s), and containing a functional group 1 and a functional group 2, which are a pair of functional groups capable of reacting to form a bond; and
   (2) cyclizing the non-cyclic peptide compound by the reaction of the functional group 1 with the functional group 2 to form a bond between said groups,
   wherein a ribozyme capable of catalyzing an aminoacylation reaction of a tRNA with a moderately activated amino acid compound having an aromatic ring is used to translationally synthesize the non-cyclic peptide compound, and
   wherein the pair of functional groups 1 and 2 is one of the following pairs (A) to (C):

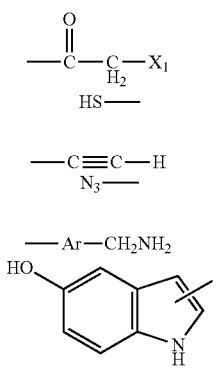

wherein $X_1$ is Cl or Br, and Ar is an aromatic ring optionally having a substituent,
wherein the step (1) comprises the substeps of:
   (a) providing the ribozyme capable of catalyzing an aminoacylation reaction of a tRNA with a moderately activated amino acid compound having an aromatic ring;
   (b) providing an initiator tRNA and an amino acid compound having the functional group 1 for use as a substrate for the acylation reaction by the ribozyme;
   (c) performing an aminoacylation of the initiator tRNA with the amino acid compound having the functional group 1 using the ribozyme;
   (d) providing a cell-free translation system which contains at least an amino acid compound having the functional group 2 and a tRNA to be aminoacylated with the amino acid compound having the functional group 2, and is free of methionine;
   (e) providing a template DNA for forming an mRNA having at desired positions a codon corresponding to an anticodon of the initiator tRNA, and a codon corresponding to an anticodon of the tRNA to be aminoacylated with the amino acid compound having the functional group 2; and
   (f) adding the aminoacylated initiator tRNA obtained in the substep (c) and the template DNA to the cell-free translation system to synthesize the non-cyclic peptide compound.

2. A process for synthesizing a cyclic peptide compound, comprising the steps of:
   (1) translationally synthesizing a non-cyclic peptide compound comprising non-natural amino acid(s), and containing a functional group 1 and a functional group 2, which are a pair of functional groups capable of reacting to form a bond; and
   (2) cyclizing the non-cyclic peptide compound by the reaction of the functional group 1 with the functional group 2 to form a bond between said groups,
   wherein a ribozyme capable of catalyzing an aminoacylation reaction of a tRNA with a moderately activated amino acid compound having an aromatic ring is used to translationally synthesize the non-cyclic peptide compound, and
   wherein the pair of functional groups 1 and 2 is one of the following pairs (A) to (C):

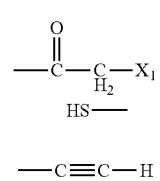

-continued

N₃——

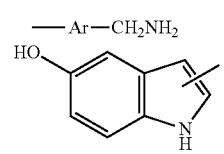

(C)

wherein X₁ is Cl or Br, and Ar is an aromatic ring optionally having a substituent, wherein the step (1) comprises the substeps of:
(a) providing the ribozyme capable of catalyzing an aminoacylation reaction of a tRNA with a moderately activated amino acid compound having an aromatic ring;
(b) providing an initiator tRNA and an amino acid compound having the functional group 1 for use as a substrate for the acylation reaction by the ribozyme;
(c) performing an aminoacylation of the initiator tRNA with the amino acid compound having the functional group 1 using the ribozyme;
(d) providing a tRNA having an orthogonal relationship to a natural aminoacyl-tRNA synthetase present in a cell-free translation system, and an amino acid compound having the functional group 2, for use as a substrate for the acylation reaction by the ribozyme;
(e) performing an aminoacylation of the tRNA with the amino acid compound having the functional group 2 using the ribozyme;
(f) providing a cell-free translation system free of methionine;
(g) providing a template DNA for forming an mRNA having at desired positions a codon corresponding to an anticodon of the initiator tRNA, and a codon corresponding to an anticodon of the tRNA; and
(h) adding the aminoacylated initiator tRNA obtained in the substep (c), the tRNA aminoacylated in the substep (e) with the amino acid compound having the functional group 2, and the template DNA to the cell-free translation system to synthesize the non-cyclic peptide compound.

3. A process for synthesizing a cyclic peptide compound, comprising the steps of:
(1) translationally synthesizing a non-cyclic peptide compound comprising non-natural amino acid(s), and containing a functional group 1 and a functional group 2, which are a pair of functional groups capable of reacting to form a bond; and
(2) cyclizing the non-cyclic peptide compound by the reaction of the functional group 1 with the functional group 2 to form a bond between said groups,
wherein a ribozyme capable of catalyzing an aminoacylation reaction of a tRNA with a moderately activated amino acid compound having an aromatic ring is used to translationally synthesize the non-cyclic peptide compound, and
wherein the pair of functional groups 1 and 2 is one of the following pairs (A) to (C):

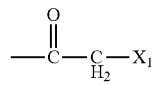

(A)

-continued

HS——

(B)

—C≡C—H

N₃——

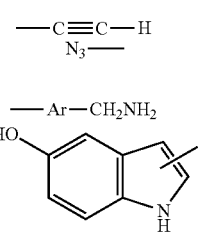

(C)

wherein X₁ is Cl or Br, and Ar is an aromatic ring optionally having a substituent, wherein the step (1) comprises the substeps of:
(a) providing the ribozyme capable of catalyzing an aminoacylation reaction of a tRNA with a moderately activated amino acid compound having an aromatic ring;
(b) providing a tRNA having an orthogonal relationship to a natural aminoacyl-tRNA synthetase present in a cell-free translation system, and an amino acid compound having the functional group 1, for use as a substrate for the acylation reaction by the ribozyme;
(c) performing an aminoacylation of the tRNA with the amino acid compound having the functional group 1 using the ribozyme;
(d) providing a cell-free translation system containing at least an amino acid compound having the functional group 2, a tRNA to be aminoacylated with the amino acid compound having the functional group 2, an initiator tRNA, methionine, and a methionyl-tRNA synthetase;
(e) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and
(f) adding the aminoacylated tRNA obtained in the substep (c) and the template DNA to the cell-free translation system to synthesize the non-cyclic peptide compound.

4. A process for synthesizing a cyclic peptide compound, comprising the steps of:
(1) translationally synthesizing a non-cyclic peptide compound comprising non-natural amino acid(s), and containing a functional group 1 and a functional group 2, which are a pair of functional groups capable of reacting to form a bond; and
(2) cyclizing the non-cyclic peptide compound by the reaction of the functional group 1 with the functional group 2 to form a bond between said groups,
wherein a ribozyme capable of catalyzing an aminoacylation reaction of a tRNA with a moderately activated amino acid compound having an aromatic ring is used to translationally synthesize the non-cyclic peptide compound, and
wherein the pair of functional groups 1 and 2 is one of the following pairs (A) to (C):

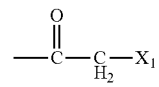

(A)

-continued

HS—

—C≡C—H
N₃— (B)

—Ar—CH₂NH₂ (C)

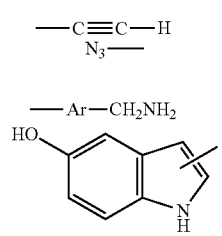

wherein X₁ is Cl or Br, and Ar is an aromatic ring optionally having a substituent, wherein the step (1) comprises the substeps of:

(a) providing the ribozyme capable of catalyzing an aminoacylation reaction of a tRNA with a moderately activated amino acid compound having an aromatic ring;

(b) providing a tRNA having an orthogonal relationship to a natural aminoacyl-tRNA synthetase present in a cell-free translation system, and an amino acid compound having the functional group 1, for use as a substrate for the acylation reaction by the ribozyme;

(c) performing an aminoacylation of the tRNA with the amino acid compound having the functional group 1 using the ribozyme;

(d) providing a tRNA having an orthogonal relationship to a natural aminoacyl-tRNA synthetase present in a cell-free translation system, and an amino acid compound having the functional group 2, for use as a substrate for the acylation reaction by the ribozyme;

(e) performing an aminoacylation of the tRNA with the amino acid compound having the functional group 2 using the ribozyme;

(f) providing a cell-free translation system containing at least an initiator tRNA, methionine, and a methionyl-tRNA synthetase;

(g) providing a template DNA for forming an mRNA having at desired positions a codon corresponding to an anticodon of the tRNA to be aminoacylated with the amino acid compound having the functional group 1, and a codon corresponding to an anticodon of the tRNA to be aminoacylated with the amino acid compound having the functional group 2; and (h) adding the aminoacylated tRNA obtained in the substep (c), the aminoacylated tRNA obtained in the substep (e), and the template DNA to the cell-free translation system to synthesize the non-cyclic peptide compound.

5. The process of claim 1, wherein the amino acid compound in the substep (b) is a compound of formula (1):

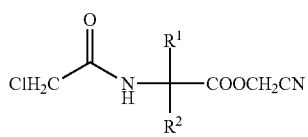

wherein R¹ and R² represent a hydrogen atom or any substituent connected by carbon; and the amino acid compound in the substep (d) is cysteine.

6. The process of claim 2, wherein the amino acid compound in the substep (b) is a compound of formula (2), and the amino acid compound in the substep (d) is a compound of formula (3):

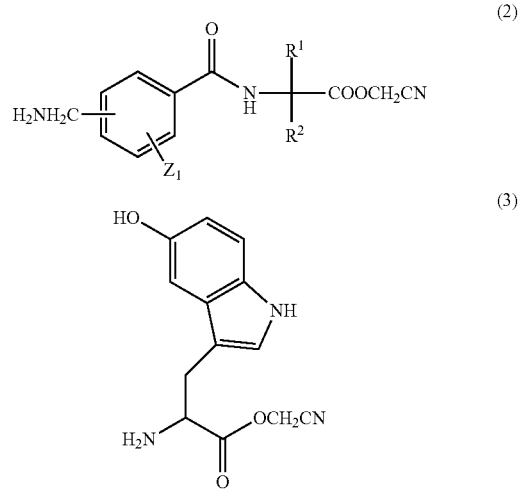

wherein R¹ and R² are as defined above, and Z₁ represents any substituent.

7. The process of claim 3, wherein the amino acid compound in the substep (b) is a compound of formula (4):

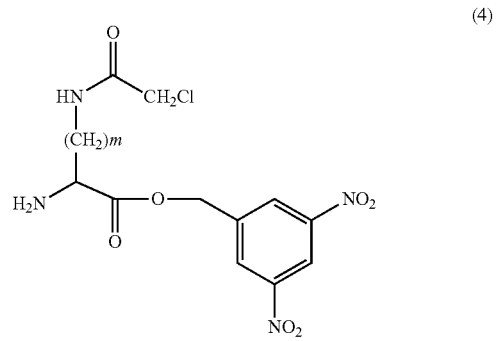

wherein m is an integer of 1 to 10; and the amino acid compound in the substep (d) is cysteine.

8. The process of claim 4, wherein the amino acid compound in the substep (b) is a compound of formula (5), and the amino acid compound in the substep (d) is a compound of formula (6):

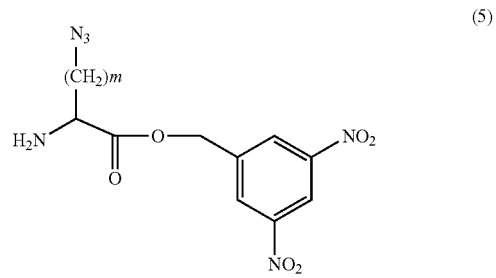

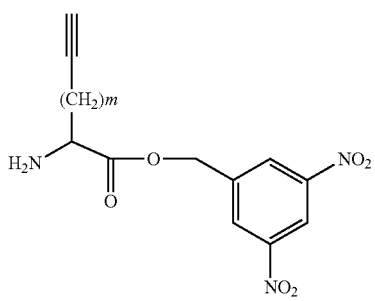

(6)

wherein m is as defined above.

9. The process of claim 4, wherein the amino acid compound in the substep (b) is a compound of formula (7), and the amino acid compound in the substep (d) is a compound of formula (8):

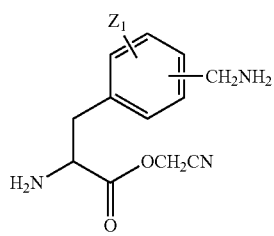

(7)

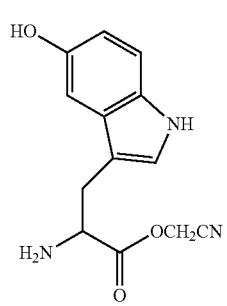

(8)

wherein $Z_1$ is as defined above.

10. The process of any one of claims 1 to 4, wherein the ribozyme capable of catalyzing the aminoacylation reaction of tRNA with a moderately activated amino acid compound having an aromatic ring consists of the base sequence (I) or (II) below:

(I)
GGAUCGAAAGAUUUCCGCGGCCCCGAAAGGGGAUUAGCGUUAGGU
(SEQ ID NO: 37)

(II)
GGAUCGAAAGAUUUCCGCAUCCCCGAAAGGGUACAUGGCGUUAGGU
(SEQ ID NO: 38).

* * * * *